United States Patent
Burt et al.

[11] Patent Number: 5,466,796
[45] Date of Patent: Nov. 14, 1995

[54] ALKOXY-BRIDGED METALLOPHTHALOCYANINE DIMERS

[75] Inventors: Richard A. Burt, Oakville; George Liebermann; Gordon K. Hamer, both of Mississauga; Sandra J. Gardner, Willowdale; Carol A. Jennings, Mississauga, all of Canada; Katsumi Daimon; Katsumi Nukada, both of Minami Ashigara, Japan

[73] Assignee: Xerox Corporation, Stamford, Conn.

[21] Appl. No.: 239,432

[22] Filed: Apr. 26, 1994

[51] Int. Cl.⁶ .................................................. C09B 47/04
[52] U.S. Cl. .......................... 540/139; 540/122; 540/140
[58] Field of Search ...................... 540/122, 139, 540/140

[56]  References Cited

U.S. PATENT DOCUMENTS

| 4,311,775 | 1/1982 | Regan | 430/37 |
| 4,900,817 | 2/1990 | Batzel et al. | 540/140 |

FOREIGN PATENT DOCUMENTS 1221459 of 1989 Japan.

OTHER PUBLICATIONS

Ercolani et al. Inorg. Chem, 25, 3972–6 1986.
Bull. Soc. Chim. Fr., 23 (1962), D. Colaitis.
J. Chem. Soc., 1717, 1936, P. A. Barrett et al.
Russ. J. Phys. Chem. (Engl. Transl.), 41, 251, 1967, I. S. Kirin et al.
Inorg. Chem. 12, 930, 1973, W. R. Bennett et al.

Primary Examiner—Mukund J. Shah
Assistant Examiner—Pavanaram K. Sripada
Attorney, Agent, or Firm—E. O. Palazzo

[57]  ABSTRACT

Alkoxy-bridged metallophthalocyanine dimers of the formula $C_{32}H_{16}N_8MOROMN_8H_{16}C_{32}$, or of the formula

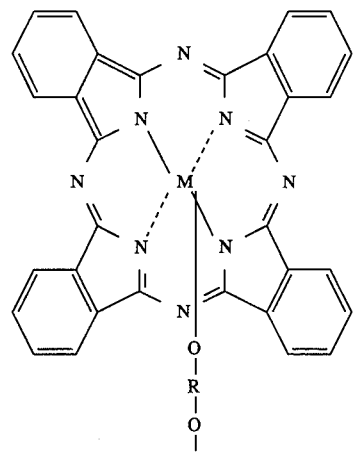
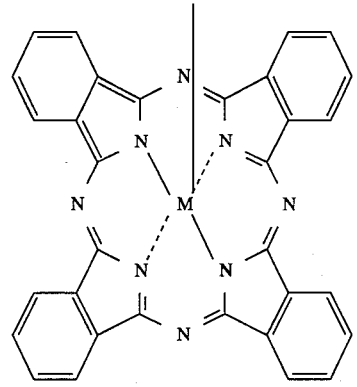

wherein M is a metal, and R is an alkyl or an alkyl ether.

23 Claims, 3 Drawing Sheets

ALKOXY-BRIDGED METALLOPHTHALOCYANINE DIMERS

BACKGROUND OF THE INVENTION

This invention is generally directed to certain phthalocyanines such as metallophthalocyanines and, more specifically, the present invention is directed to alkoxy-bridged metallophthalocyanine dimers, processes thereof, and photoconductive imaging members thereof. In embodiments, the present invention is directed to novel metallophthalocyanine dimers, such as alkoxy-bridged metallophthalocyanine dimers of a trivalent metal of the following Formula 1 wherein the substituents are as illustrated herein

FORMULA 1

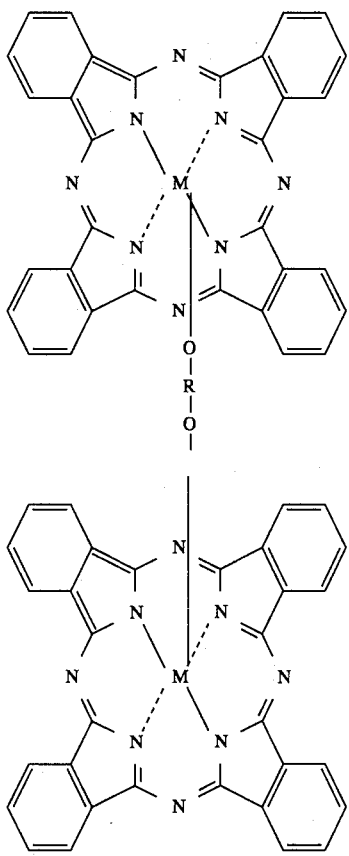

that is M is a metal, and R is an alkyl group or an alkyl ether.

Also in embodiments, the present invention is directed to specific alkoxy-bridged metallophthalocyanine dimers, including alkoxy-bridged gallium phthalocyanine dimers. The alkoxy-bridged metallophthalocyanine dimers of the present invention can be obtained by the reaction of ortho-phthalodinitrile or 1,3-diiminoisoindoline with complexes of trivalent metals, such as the alkoxides, acetates or acetylacetonates, in the presence of a dialcohol (diol).

The resulting alkoxy-bridged metallophthalocyanine dimers, such as alkoxy-bridged galliumphthalocyanine dimers can be selected for utilization in layered photoconductive imaging members, including those that possess infrared photosensitivity, for example from about 700 to about 850 nanometers, and wherein the dimer is selected as the photogenerating pigment. The formed dimer can be selected as the photogenerating pigment or the dimer can be converted to the corresponding hydroxy metallophthalocyanine which phthalocyanines may be selected as the photogenerating pigment.

In embodiments, trivalent metal alkoxides can be obtained from the reaction of the corresponding trivalent metal halide with an alkali metal salt of an alcohol (alkali metal alkoxide), and the alkali metal halide byproduct formed may be removed by filtration. In embodiments, the trivalent metal alkoxides can alternatively be obtained from the reaction of the corresponding trivalent metal halide with an alcohol in the presence of a base such as ammonia, and the ammonium halide byproduct formed may be removed by filtration. Once formed, the trivalent metal alkoxide can be separated from the halide byproduct, or it may be utilized in situ in the subsequent reaction with a diol to form the alkoxy-bridged metallophthalocyanine dimer. In embodiments, the trivalent metal alkoxide can be prepared by reacting a gallium halide, especially the chloride, and an alkali metal alkoxide, and thereafter reacting the resulting gallium alkoxide with, for example, phthalodinitrile or 1,3-diiminoisoindoline in the presence of a diol, plus an optional organic solvent like N-methylpyrrolidone, a halonaphthalene like 1-chloronaphthalene, quinoline, and the like to form the alkoxy-bridged galliumphthalocyanine dimer. Further, in embodiments the process of the present invention comprises the reaction of a trivalent metal halide like gallium trichloride with an aliphatic alcohol like butanol in the presence of a base, such as ammonia, and subsequently reacting the resulting gallium butoxide with, for example, ortho-phthalodinitrile or 1,3-diiminoisoindoline in the presence of a diol, and an optional organic solvent to form the alkoxy-bridged galliumphthalocyanine dimer. The aforementioned and other processes for the preparation of dimers and trivalent metal alkoxide and imaging members thereof are illustrated in copending patent applications U.S. Ser. No. 233,834, U.S. Ser. No. 233,832, U.S. Serial No. 233,195, the disclosures of which are totally incorporated herein by reference.

The alkoxy-bridged metallophthalocyanine dimers, or the corresponding hydroxy metal phthalocyanines obtained from the hydrolysis of the dimer, such as hydroxy gallium phthalocyanine Type V can be selected as organic photogenerator pigments in layered photoresponsive imaging members with charge transport layers, especially hole transport layers containing hole transport molecules such as known tertiary aryl amines. The aforementioned photoresponsive, or photoconductive imaging members can be negatively charged when the photogenerating layer is situated between the hole transport layer and the substrate, or positively charged When the hole transport layer is situated between the photogenerating layer and the supporting substrate. The layered photoconductive imaging members can be selected for a number of different known imaging and printing processes including, for example, electrophotographic imaging processes, especially xerographic imaging and printing processes wherein negatively charged or positively charged images are rendered visible using toner compositions of appropriate charge polarity. In general, the imaging members are sensitive in the wavelength region of from about 550 to about 900 nanometers, and in particular, from about 700 to about 850 nanometers, thus diode lasers can be selected as the light source.

In embodiments, the alkoxy-bridged metallophthalocyanine dimers, such as alkoxy-bridged galliumphthalocyanine dimers of the present invention, can be selected as photogenerator pigments in photoresponsive imaging members. These photoresponsive imaging members may be layered photoconductive imaging members, and may contain separate charge transport layers, especially hole transport layers containing hole transport molecules. The imaging members containing alkoxy-bridged metallophthalocyanine dimers possess infrared photosensitivity and are sensitive in the wavelength regions of from about 650 to about 850 nanometers, therefore, diode lasers can be selected as the light source. The layered photoconductive imaging members can be selected for a number of different known imaging and printing processes including, for example, electrophotographic imaging processes, especially xerographic imaging and printing processes wherein negatively charged or positively charged images are rendered visible using toner compositions of appropriate charge polarity. The alkoxy-bridged metallophthalocyanine dimers can also be selected as precursors for the preparation of other phthalocyanines, such as hydroxy metallophthalocyanines, which phthalocyanines may be selected as a photogenerating pigment in photoresponsive imaging members.

The present invention is also directed to efficient synthetic methods for obtaining alkoxy-bridged metallophthalocyanine dimers by utilizing trivalent metal alkoxides obtained from metal halides as indicated herein. Alkoxy-bridged metallophthalocyanine dimers can be obtained by the reaction of ortho-phthalodinitrile or 1,3-diiminoisoindoline with a trivalent metal alkoxide in the presence of a diol. During the aforementioned reaction, the diol, which can also act as a solvent for the reaction, is chemically incorporated into the phthalocyanine product with the formation of an alkoxy-bridged metallophthalocyanine dimer of the formula $C_{32}H_{16}N_8MOROMN_8H_{16}C_{32}$ as illustrated herein, wherein M is a trivalent metal, and the alkoxy bridge (O-R-O) contains the diol moiety (R). The alkoxy-bridged metallophthalocyanine dimers can also be obtained by the reaction of ortho-phthalodinitrile or 1,3-diiminoisoindoline with other complexes of trivalent metals, such as the acetates and acetylacetonates, in the presence of a diol. Alternatively, the alkoxy-bridged metallophthalocyanine dimers can be prepared by the reaction of hydroxy metallophthalocyanines of a trivalent metal with a diol, in the presence of excess diol or another solvent.

In embodiments the present invention is also directed to an efficient and economical process for the preparation of alkoxy-bridged metallophthalocyanine dimers by the in situ formation of trivalent metal alkoxides from metal halides. The metal halides are about one-tenth the cost and readily available from various sources such as APL Engineered Material, Urbana, Ill. and Gallard Schlesinger Industries, Carle Place, N.Y., which supply specific inorganic or organometallic chemicals on multi kilogram scale from stock supplies, compared to the corresponding trivalent metal alkoxides, acetates and acetylacetonates, which are usually special order produced on less than one kilogram scale. Thus, the alkoxy-bridged metallophthalocyanine dimers of the present invention can be prepared in efficient, economical and high yield, 70 to 85 percent, synthesis from metal halides:

Certain phthalocyanines, and especially metal phthalocyanines, can be selected as pigments and colorants in printing inks, paints, coatings, plastics, catalysts, chemical sensors, electrophotography, especially xerography wherein the phthalocyanines function as photogenerating pigments, laser sensitive materials for information storage systems, electrochromic display devices, and photobiology.

Specific metallophthalocyanines containing two phthalocyanine rings in the molecule have been described in the literature. In P.A. Barrett et al. in *J. Chem Soc.*, 1717, 1936, there is illustrated $(AlPc)_2O$, a μ-oxo bridged aluminum phthalocyanine of Formula 2.

FORMULA 2

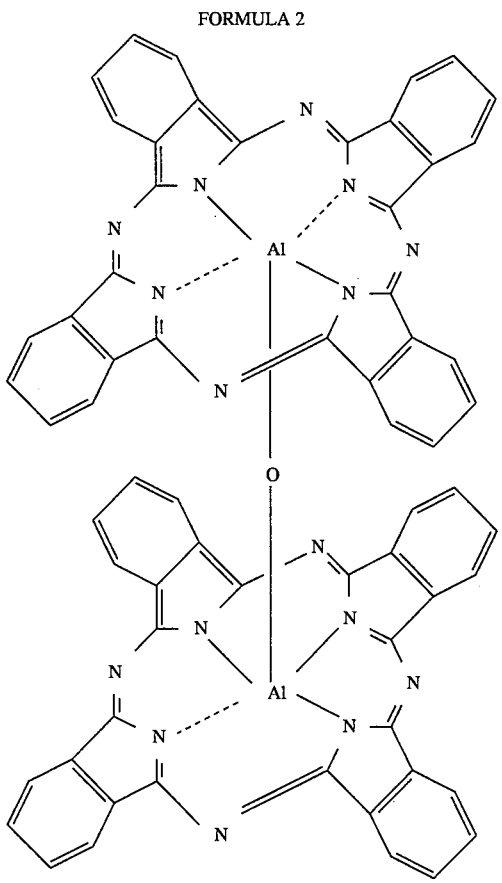

The formation of a similar compound of trivalent Fe, $(FePc)_2O$ by aeration of FePc was described by C. Ercolani et al. in *Inorg. Chem.*, 25, 3972, 1986.

Bis(phthalocyaninato)lanthanide(III) complexes, also described as lanthanide diphthalocyanines $[L(Pc)_2]$ were reported by I.S. Kirin et al. in *Russ. J. Phys. Chem* (Engl Transl), 41,251, 1967. The lutetium phthalocyanine dimer was well studied according to the literature, for example for its electrochromic properties. *Phthalocyanines Properties and Applications*, 1989, VCH Publishers, Inc., edited by C.C. Leznoff and A.B.P. Lever, describes a series of these materials with the corresponding original references thereto.

Diphthalocyanines of tetravalent metals, such as stanium, $Sn(Pc)_2$, and zirconium, $Zr(Pc)_2$, of the structure shown in Formula 3, have been synthesized and described by W.R. Bennet et al. in *Inorg Chem.* 12, 930, 1973 and J. Silver et al. in *Polyhedron*, 8, 1631, 1989.

FORMULA 3

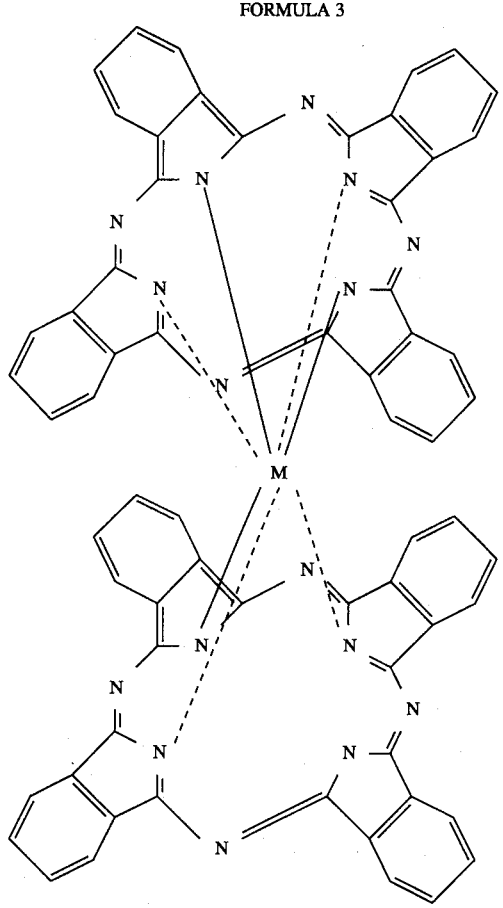

In the aforementioned documents there is no disclosure, it is believed, of the alkoxy-bridged metallophthalocyanine dimers of the present invention, such as alkoxy-bridged gallium phthalocyanine dimers, and their use as photogenerating pigments, as precursors, for example, in the preparation of hydroxygallium Type V phthalocyanines, or for the preparation of other phthalocyanine compounds, such as hydroxymetallo phthalocyanines, as illustrated in copending application U.S. Ser. No. 233,834, the disclosure of which is totally incorporated herein by reference.

Many halometallo- and hydroxymetallo phthalocyanines of trivalent metals, such as Al, Ga and In, are described in the literature, for example in *The Phthalocyanines*, vols. I and II, F.H. Moser and A.L. Thomas, CRC Press Inc., 1983 and by J.P. Linsky et al. in *Inorg. Chem.* 19, 3131, 1980.

In *Bull. Soc. Chim. Fr.*, 23 (1962), there is illustrated the preparation of chlorogallium phthalocyanine by reaction of o-cyanobenzamide with gallium chloride in the absence of solvent, and hydroxygallium phthalocyanine by dissolution of chlorogallium phthalocyanine in concentrated sulfuric acid, followed by reprecipitation in diluted aqueous ammonia. Further, there are illustrated in JPLO 1-221459 (Toyo Ink Manufacturing) processes for preparing chlorogallium phthalocyanines and hydroxygallium phthalocyanines, as well as photoreceptors for use in electrophotography. A number of hydroxygallium phthalocyanine polymorphs and processes for the preparation thereof are described in JPLO 5-263007, the disclosure of which is totally incorporated herein by reference.

Further, hydroxygallium phthalocyanine is generally obtained by the hydrolysis of chlorogallium phthalocyanine. Ring chlorination often occurs in the preparation of chlorogallium phthalocyanine because gallium chloride is used at high temperature in the phthalocyanine synthesis, and this can effect the purity of the final product. This chlorine incorporation can result in detrimental properties when the phthalocyanine is used in special high purity applications such as electrophotography. This problem can be avoided by using an alkoxy-bridged gallium phthalocyanine dimer as the precursor. The alkoxy-bridged gallium phthalocyanine dimer can be hydrolyzed to hydroxygallium phthalocyanine by standard methods, such as by treatment with sulfuric acid, using a procedure similar to that described for the hydrolysis of chlorogallium phthalocyanine in *Bull. Soc. Chim. Fr.*, 23 (1962). The hydroxygallium phthalocyanine can then be converted to the photosensitive Type V polymorph as described in copending application U.S. Ser. No. 233,834. By using an alkoxy-bridged gallium phthalocyanine dimer precursor in the preparation of Type V hydroxygallium phthalocyanine, any negative effects of residual chlorine, or ring chlorination, such as higher dark decay and higher cycle down, are avoided or minimized.

The alkoxy-bridged metallophthalocyanine dimers, shown by Formula 1 and described herein, are considered novel phthalocyanine dimers, or diphthalocyanines, which have an alkoxy bridge (O-R-O-) linking the two metal atoms of the metallophthalocyanine rings. The structure between the two oxygen molecules of the bridge is determined by the diol used in the synthesis. The trivalent metal in the phthalocyanine dimer structure can be selected from a number of components, such as aluminum, gallium or indium, or trivalent transitional metals, such as Mn(III), Fe(III), Co(III), Ni(III), Cr(III), and the like. In embodiments, this invention relates to alkoxy-bridged gallium phthalocyanine dimers as representatives of the new class of alkoxy-bridged metallophthalocyanine dimers.

Further, there is illustrated in JPLO 221459 a photoreceptor for use in electrophotography comprising a charge generation material and charge transport material on a conductive substrate, and wherein the charge generation material comprises one or a mixture of two or more of gallium phthalocyanine compounds which evidence the following intense diffraction peaks at Bragg angles (2 theta+/−0.2°) in the X-ray diffraction spectrum, 1-6.7, 15.2, 20.5, 27.0

2-6.7, 13.7, 16.3, 20.9, 26.3

3-7.5, 9.5, 11.0, 13.5, 19.1, 20.3, 21.8, 25.8, 27.1,33.0.

In Konica Japanese 64-17066/89, there is disclosed, for example, the use of a new crystal modification of titanyl phthalocyanine (TiOPc) prepared from alpha-type TiOPc (Type II) by milling it in a sand mill with salt and polyethylene glycol. This publication also discloses that this new polymorph differs from alpha-type pigment in its light absorption and shows a maximum absorbance at 817 nanometers while the alpha-type exhibits a maximum at 830 nanometers. The Konica publication also discloses the use of this new form of TiOPc in a layered electrophotographic device having high photosensitivity at exposure radiation of 780 nanometers. Further, this new polymorph of TiOPc is also described in U.S. Pat. No. 4,898,799 and in a paper presented at the Annual Conference of Japan Hardcopy in Jul. 1989. In this paper, this same new polymorph is referred to as Type Y, and reference is also made to Types I, II, and III as A, B, and C, respectively. Also, in U.S. Serial No. 169,486 (D/93427), the disclosure of which is totally incorporated herein by reference, there is illustrated a process for the preparation of hydroxygallium phthalocyanine Type V, essentially free of chlorine, whereby a pigment precursor Type I chlorogallium phthalocyanine is prepared by reaction of gallium chloride in a solvent, such as N-methylpyrrolidone, present in an amount of from about 10 parts to about 100 parts, and preferably about 19 parts, with 1,3-diiminoisoindoline ($DI^3$) in an amount of from about 1 part to about 10 parts, and preferably about 4 parts $DI^3$ for each part of gallium chloride that is reacted; hydrolyzing said pigment precursor chlorogallium phthalocyanine Type I by standard methods, for example acid pasting, whereby the pigment precursor is dissolved in concentrated sulfuric acid and then reprecipitated in a solvent, such as water, or a dilute ammonia solution, for example from about 10 to about 15 percent; and subsequently treating the resulting hydrolyzed pigment hydroxygallium phthalocyanine Type I with a solvent, such as N,N-dimethylformamide, present in an amount of from about 1 volume part to about 50 volume parts and preferably about 15 volume parts for each weight part of pigment hydroxygallium phthalocyanine that is used by, for example, ball milling said Type I hydroxygallium phthalocyanine pigment in the presence of spherical glass beads, approximately 1 millimeter to 5 millimeters in diameter, at room temperature, about 25 degrees, for a period of from about 12 hours to about 1 week, and preferably about 24 hours such that there is obtained a hydroxygallium phthalocyanine Type V, contains very low levels of residual chlorine of from about 0.001 percent to about 0.1 percent, and in an embodiment about 0.03 percent of the weight of the Type V hydroxygallium pigment, as determined by elemental analysis.

Further, in U.S. Pat. No. 5,407,766, the disclosure of which is totally incorporated herein by reference, there is illustrated a process for the preparation of hydroxygallium phthalocyanine Type V, which comprises formation of a precursor of gallium phthalocyanine, prepared by reaction of 1,3-diiminoisoindoline with gallium acetylacetonate in a suitable solvent; hydrolyzing the precursor by dissolving in a strong acid and then reprecipitating the dissolved pigment in aqueous ammonia, thereby forming Type I hydroxygallium phthalocyanine; and admixing the Type I hydroxygallium phthalocyanine with a polar aprotic organic solvent; and more specifically a process for the preparation of Type V hydroxy gallium phthalocyanine, which comprises preparing a precursor gallium phthalocyanine by the reaction of 1,3-diiminoisoindoline with gallium acetylacetonate in a suitable solvent; filtering and thereafter washing the pigment precursor gallium phthalocyanine with hot N,N-dimethylformamide, followed by washing with an organic solvent, such as methanol or acetone; hydrolyzing said precursor by dissolving in a strong acid and then reprecipitating the dissolved pigment in aqueous ammonia, thereby forming Type I hydroxygallium phthalocyanine; and admixing the Type I with the organic solvent N,N-dimethylformamide.

In copending patent applications filed concurrently herewith, there is illustrated in U.S. Ser. No. 233,834 a process for the preparation of Type V hydroxygallium phthalocyanine which comprises the in situ formation of an alkoxy-bridged gallium phthalocyanine dimer, hydrolyzing said alkoxy-bridged gallium phthalocyanine dimer to hydroxygallium phthalocyanine, and subsequently converting the hydroxygallium phthalocyanine product obtained to Type V hydroxygallium phthalocyanine; and a process for the preparation of Type V hydroxygallium phthalocyanine which comprises the formation of an alkoxy-bridged gallium phthalocyanine dimer by the reaction of an organic gallium complex with ortho-phthalodinitrile or 1,3-diiminoisoindoline and a diol; hydrolyzing the resulting alkoxy-bridged gallium phthalocyanine dimer to hydroxygallium phthalocyanine, and subsequently converting the hydroxygallium phthalocyanine product obtained to Type V hydroxygallium phthalocyanine; U.S. Ser. No. 233,832 a photoconductive imaging member comprised of an alkoxy-bridged metallophthalocyanine dimer as a charge generator material, wherein the dimer is of the formula $C_{32}H_{16}N_8MOROMN_8H_{16}C_{32}$ wherein M is a trivalent metal, and R is an alkyl group or an alkyl ether group

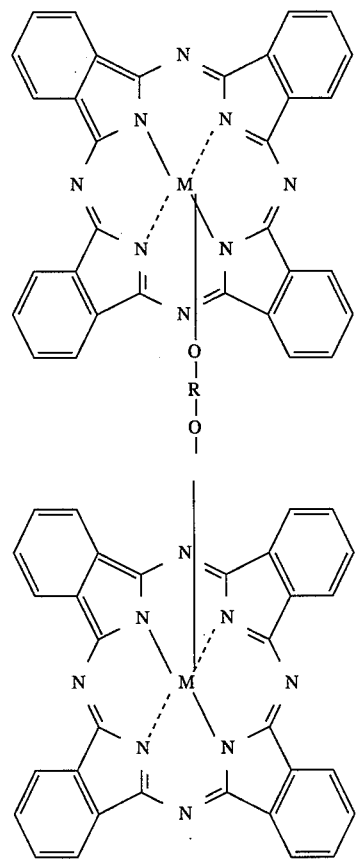

and U.S. Ser. No. 233,195 a process for the preparation of alkoxy-bridged metallophthalocyanine dimers by the reaction of a trivalent metal compound with ortho-phthalodinitrile or 1,3-diiminoisoindoline in the presence of a diol.

The disclosures of all of the aforementioned publications, laid open applications, copending applications and patents are totally incorporated herein by reference.

SUMMARY OF THE INVENTION

It is an object of the present invention to provide processes for the preparation of novel alkoxy-bridged metallophthalocyanine dimers and imaging members thereof with many of the advantages illustrated herein.

Another object of the present invention is to provide alkoxy-bridged metallophthalocyanine dimers and imaging members thereof with many of the advantages illustrated herein.

Further, another object of the present invention is to provide hydroxy metallophthalocyanines from alkoxy-bridged metallophthalocyanine dimers and imaging members with hydroxy metallophthalocyanines with many of the advantages illustrated herein.

Another object of the present invention relates to the provision of improved layered photoresponsive imaging members with photosensitivity to near infrared radiations.

It is yet another object of the present invention to provide simple and economical processes for the preparation of gallium phthalocyanines.

Also, it is an object of the present invention to provide a new class of phthalocyanines referred to as alkoxy-bridged metallophthalocyanine dimers.

Another object of the present invention is to provide alkoxy-bridged metallophthalocyanine dimers that can be selected as photogenerating pigments in photoconductive imaging members.

It is yet another object of the present invention to provide alkoxy-bridged metallophthalocyanine dimers useful as precursors in the preparation of other polymorphs or other phthalocyanines.

Another object of the present invention is to provide photogenerating pigments of alkoxy-bridged metallophthalocyanine dimers of the formula $C_{32}H_{16}N_8MOROMN_8H_{16}C_{32}$ wherein the metal M is selected from trivalent metals such as aluminum, gallium, indium, or other metals in a trivalent form, and R is an aliphatic group like alkyl.

It is another object of the present invention to provide alkoxy-bridged metallophthalocyanine dimers of the formula $C_{32}H_{16}N_8MOROMN_8H_{16}C_{32}$ wherein R is a moiety provided by the diol used in the preparation of the phthalocyanine dimer, and M is a metal.

A further object of the present invention is to provide alkoxy-bridged galliumphthalocyanine dimers of the formula $C_{32}H_{16}N_8GaOROGaN_8H_{16}C_{32}$ wherein R is a moiety provided by the diol used in the preparation of the phthalocyanine dimer.

A further object of the present invention is to provide alkoxy-bridged galliumphthalocyanine dimers obtained by accomplishing the phthalocyanine syntheses in different diol solvents which result in the formation of the corresponding alkoxy-bridged gallium phthalocyanine dimers. Thus, for example, using 1,2-ethanediol (ethylene glycol) as reactant and as reaction solvent for the alkoxy-bridged gallium phthalocyanine dimer synthesis provides the dimer which incorporates the ethanediol fragment into the structure and has the specific formula $C_{32}H_{16}N_8GaOCH_2CH_2OGaN_8H_{16}C_{32}$.

It is yet another object of the present invention to provide simple and economical processes for the preparation of gallium phthalocyanines.

In a further object of the present invention there are provided processes for the preparation of Type V hydroxygallium phthalocyanine with an XRPD with peaks at Bragg angles of 7.4, 9.8, 12.4, 16.2, 17.6, 18.4, 21.9, 23.9, 25.0, 28.1, and the highest peak at 7.4 degrees 2Θ.

Additionally, in another object of the present invention there is provided a two step process for the preparation of alkoxy-bridged metallophthalocyanine dimers and imaging members thereof.

In yet a further object of the present invention there is provided a one step in situ process for the preparation of alkoxy-bridged metallophthalocyanine dimers.

Also, in yet a further object of the present invention there are provided processes for the preparation of hydroxy metallophthalocyanines from alkoxy-bridged metallophthalocyanine dimers.

In a further object of the present invention there are provided processes for the preparation of trivalent metal alkoxides from the metal chloride for use in the synthesis of alkoxy-bridged metallophthalocyanine dimers, wherein the use of the trivalent metal chloride directly for the phthalocyanine synthesis is avoided, and which metal alkoxides can be selected as a reactant for the processes of the present invention either in situ or in a two step reaction.

A further object of the present invention relates to the preparation of electrically pure alkoxy-bridged metallophthalocyanine dimers in acceptable yield, for example from about 30 percent to about 90 percent, and in embodiments about 80 percent.

In still a further object of the present invention there are provided photoresponsive imaging members with an aryl amine hole transport layer, and a photogenerator layer comprised of alkoxy-bridged metallophthalocyanine dimers, the corresponding hydroxy metallophthalocyanines, or mixtures thereof as photogenerating pigment components.

DESCRIPTION OF THE EMBODIMENTS

These and other objects of the present invention can be accomplished in embodiments thereof by the provision of alkoxy-bridged metallophthalocyanine dimers, the corresponding hydroxy metallophthalocyanines, processes for the preparation thereof, and imaging members thereof.

More specifically, the present invention is directed to alkoxy-bridged metallophthalocyanine dimers of the formula $C_{32}H_{16}N_8MOROMN_8H_{16}C_{32}$, or

FORMULA 1

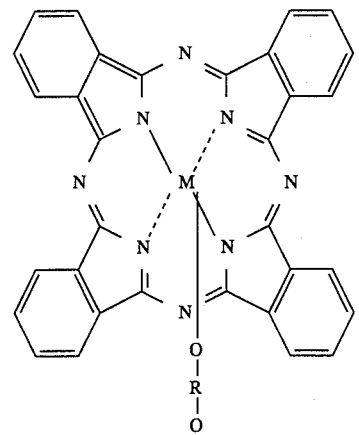

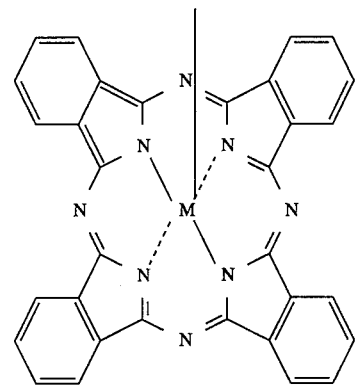

wherein M is a trivalent metal, and R is an alkyl group or an alkyl ether originating from the diol (HO-R-OH) used in the preparation of the dimer such as known ethers with ethyl, propyl and butyl groups.

In embodiments, M is a trivalent metal such as aluminum, gallium or indium, or a trivalent transition metal such as Fe(III), Cr(III), Co(III), Mn(III), Ni(III), or V(III);

R is an alkyl group with 2 to about 12, and preferably 2 to about 6 carbon atoms such as methyl, ethyl, propyl, butyl, pentyl, hexyl, octyl, nonyl, and the like, and in embodiments $$-(CH_2)_n-$$

wherein n represents the number of segments and can be, for example, a number of from 2 to about 12;

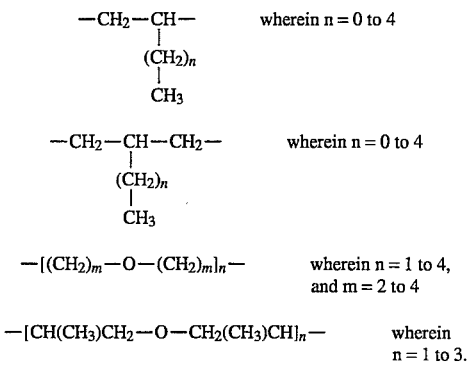

$$-CH_2-CH- \atop \underset{CH_3}{(CH_2)_n}$$ wherein n = 0 to 4

$$-CH_2-CH-CH_2- \atop \underset{CH_3}{(CH_2)_n}$$ wherein n = 0 to 4

$$-[(CH_2)_m-O-(CH_2)_m]_n-$$ wherein n = 1 to 4, and m = 2 to 4

$$-[CH(CH_3)CH_2-O-CH_2(CH_3)CH]_n-$$ wherein n = 1 to 3.

Examples of the dimers of the present invention include 1,2odi(oxoaluminum phthalocyaninyl) ethane, 1,2-di(oxogallium phthalocyaninyl) ethane, 1,2-di(oxoindium phthalocyaninyl) ethane, 1,3-di(oxoaluminum phthalocyaninyl) propane, 1,3-di(oxogallium phthalocyaninyl) propane, 1,3-di(oxoindium phthalocyaninyl) propane, 1,2-di(oxoaluminum phthalocyaninyl) propane, 1,2-di(oxogallium phthalocyaninyl) propane, and 1,2-di(oxoindium phthalocyaninyl) propane.

In embodiments of the present invention, there are provided processes for the preparation of alkoxy-bridged metallophthalocyanine dimers encompassed by Formula 1; different metals and different diols provide a number of various possible structures by the reaction of a trivalent metal alkoxide with ortho-phthalodinitrile or 1,3-diiminoisoindoline and a diol, or processes for alkoxy-bridged gallium phthalocyanine dimers of the formula illustrated herein by the reaction of a gallium complex, such as gallium alkoxide, with ortho-phthalodinitrile or 1,3-diiminoisoindoline, and a diol. The alkoxy-bridged gallium phthalocyanine dimer formed is of the general formula $C_{32}H_{16}N_8GaOROGaN_8H_{16}C_{32}$ with, for example, from 2 to about 12, and preferably about 2 to 6 carbon atoms in the alkoxy bridge (O-R-O). Embodiments of the present invention are directed to the preparation of alkoxy-bridged gallium phthalocyanine dimers, which comprise the dissolution of 1 part of a gallium trihalide, and preferably gallium trichloride in about 1 part to 100 parts, and preferably about 10 parts of an organic solvent, such as benzene, toluene, xylene or the like, at a temperature of from about 0° to about 100° C., and preferably at a temperature of about 25° C. to form a solution of the gallium trichloride; followed by the addition of 3 parts of an alkali metal alkoxide, such as sodium methoxide, sodium ethoxide, sodium propoxide or the like, preferably in a solution form, to provide a gallium alkoxide solution, and an alkali metal salt byproduct, for example sodium chloride, at a temperature of from about 0° C. to about 100° C., and preferably at a temperature of about 20° C. to about 40° C.; followed by the reaction with from about 1 part to about 10 parts, and preferably about 4 parts of ortho-phthalodinitrile or 1,3-diiminoisoindoline, and a diol, such as 1,2-ethanediol (ethylene glycol), 1,2-propanediol (propylene glycol) or 1,3-propanediol, in an amount of from about 3 parts to about 100 parts, and preferably about 10 parts for each part of the gallium alkoxide formed at a temperature of from about 150° C. to about 220° C., and preferably at a temperature of 195° C. for a period of 30 minutes to 6 hours, and preferably about 2 hours to provide an alkoxy-bridged gallium phthalocyanine dimer; which pigment is isolated by filtration at a temperature of about 20° C. to about 180° C., and preferably at about 120° C, to provide a dark blue solid identified by elemental analysis, infrared spectroscopy, proton NMR spectroscopy and XRD.

Also, in embodiments of the present invention there are provided methods for the preparation of alkoxy-bridged gallium phthalocyanine dimers by the reaction of gallium acetate or gallium acetylacetonate with ortho-phthalodinitrile or 1,3-diiminoisoindoline, and a diol. The alkoxy-bridged gallium phthalocyanine dimer formed is of the same general formula $C_{32}H_{16}N_8GaOROGaN_8H_{16}C_{32}$ with, for example, from 2 to about 12, and preferably about 2 to 6 carbon atoms in the alkoxy bridge (O-R-O). Embodiments of the present invention are directed to the preparation of alkoxy-bridged gallium phthalocyanine dimers, which comprise the reaction of 1 part of gallium acetate or gallium acetylacetonate with from about 1 part to about 10 parts, and preferably about 4 parts of ortho-phthalodinitrile or 1,3-diiminoisoindoline, and a diol, such as 1,2-ethanediol (ethylene glycol), in an amount of from about 3 parts to about 100 parts, and preferably about 10 parts for each part of the gallium compound used at a temperature of from about 150° C. to about 220° C., and preferably at a temperature of 195° C. for a period of 30 minutes to 6 hours, and preferably about 2 hours to provide an alkoxy-bridged gallium phthalocyanine dimer; which dimer photogenerating pigment is isolated by filtration at a temperature of about 20° C. to about 180° C., and preferably at about 120° C. to provide a dark blue solid identified by elemental analysis, infrared spectroscopy, proton NMR spectroscopy and XRD.

In embodiments, a trivalent metal alkoxide can be obtained from the reaction of the corresponding metal trihalide with an alkali metal salt of an alcohol, such as sodium ethoxide, in a solvent. The formed trivalent metal alkoxide can be separated from the alkali metal halide byproduct by filtration, or the mixture may be utilized in situ in the subsequent reaction to form the alkoxy-bridged metallophthalocyanine dimer.

The trivalent metal alkoxide can also be obtained from the reaction of the corresponding metal trihalide with an alcohol in the presence of a base, such as ammonia, and a solvent, such as methylene chloride. The formed trivalent metal alkoxide can be separated from the ammonium halide byproduct by filtration, or the mixture may be utilized in situ in the subsequent reaction to form the alkoxy-bridged metallophthalocyanine dimers.

Also, embodiments of the present invention are directed to the preparation of alkoxy-bridged gallium phthalocyanine dimers, which comprise the dissolution of 1 part of a gallium trihalide, and preferably gallium trichloride in about 1 part to 100 parts, and preferably about 10 parts of an organic solvent, such as benzene, toluene, xylene or the like, at a temperature of from about 0° C. to about 100° C., and preferably at a temperature of about 25° C. to form a solution of the gallium trichloride; followed by the addition of an alcohol, such as ethanol or butanol, in about 1 part to 10 parts, and preferably about 3 parts (by weight); followed by the addition of 3 parts of an amine, such as ammonia or triethylamine or the like at a temperature of from about 0° C. to about 60° C., and preferably at a temperature of about 25° C. to provide a gallium alkoxide solution and an ammonium halide salt byproduct, for example ammonium chloride; followed by the reaction with from about 1 part to about 10 parts, and preferably about 4 parts of ortho-phthalodinitrile or 1,3-diiminoisoindoline, and a diol, such as 1,2-ethanediol (ethylene glycol), in an amount of from about 3 parts to about 100 parts, and preferably about 10 parts for each part of the gallium alkoxide formed, at a temperature of from about 150° C. to about 220° C., and preferably at a temperature of 195° C. for a period of 30 minutes to 6 hours, and preferably about 2 hours to provide an alkoxy-bridged gallium phthalocyanine dimer; which dimer pigment is isolated by filtration at a temperature of about 20° C. to about 180° C., and preferably at about 120° C. to give a dark blue solid identified by elemental analysis, infrared spectroscopy, proton NMR spectroscopy and XRD.

In embodiments, the gallium alkoxide can be prepared by reacting a gallium trihalide, especially the trichloride, with an alkali metal metal alkoxide, and thereafter reacting the resulting gallium alkoxide with, for example, ortho-phthalodinitrile or 1,3-diiminoisoindoline, and a dialcohol (diol) to form the alkoxy-bridged gallium phthalocyanine dimers. The diol may also serve as a reaction solvent, or an organic solvent may be also used, such as N-methylpyrrolidone, halonaphthalenes like 1-chloronaphthalene, quinoline, and the like.

Further, embodiments of the present invention are directed to the preparation of alkoxy-bridged gallium phthalocyanine dimers, which comprise the dissolution of 1 part of a gallium trihalide, and preferably gallium trichloride in about 1 part to 100 parts, and preferably about 10 parts of an organic solvent, such as benzene, toluene, xylene or the like, at a temperature of from about 0° C. to about 100° C., and preferably at a temperature of about 25° C. to form a solution of the gallium trichloride; followed by the addition of 3 parts of an alkali metal alkoxide, such as sodium methoxide, sodium ethoxide, sodium propoxide or the like, preferably in a solution form to provide a gallium alkoxide solution, and an alkali metal salt byproduct, for example sodium chloride, at a temperature of from about 0° C. to about 100° C., and preferably at a temperature of about 20° C. to about 40° C.; followed by the reaction with from about 1 part to about 10 parts, and preferably about 4 parts of ortho-phthalodinitrile or 1,3-diiminoisoindoline, and a diol, such as 1,2-ethanediol (ethylene glycol), in an amount of from about 1 part to about 20 parts, and preferably about 5 parts for each part of the gallium alkoxide formed, and an additional organic solvent, such as N-methylpyrrolidone, a halonaphthalene like 1-chloronaphthalene, quinoline, and the like, in an amount of from about 5 parts to about 20 parts, and preferably about 10 parts at a temperature of from about 150° C. to about 220° C., and preferably at a temperature of 195° C. for a period of 30 minutes to 6 hours, and preferably about 2 hours to provide an alkoxy-bridged gallium phthalocyanine dimer; which dimer pigment is isolated by filtration at a temperature of about 20° C. to about 180° C., and preferably at about 120° C. to give a dark blue solid identified by elemental analysis, infrared spectroscopy, proton NMR spectroscopy and XRD.

In preferred embodiments, the gallium alkoxide can be prepared by reacting gallium trichloride with a sodium alkoxide, such as methoxide or ethoxide, and thereafter reacting the resulting gallium alkoxide with, for example, ortho-phthalodinitrile or 1,3-diiminoisoindoline, and a dialcohol (diol) to form the alkoxy-bridged gallium phthalocyanine dimers. Other embodiments of the present invention are directed to the preparation of alkoxy-bridged gallium phthalocyanine dimers, which comprise the dissolution of 1 part of gallium trichloride in about 1 part to 100 parts, and preferably about 10 parts of an organic solvent, such as benzene, toluene, xylene or the like, at a temperature of from about 0° C. to about 100° C., and preferably at a temperature of about 25° C. to form a solution of the gallium trichloride; followed by the addition of 3 parts of sodium methoxide, preferably in a solution form to provide a gallium methoxide solution, and a sodium chloride byproduct at a temperature of from about 0° C. to about 100° C., and preferably at a temperature of about 20° C. to about 40° C.; followed by the reaction with from about 1 part to about 10 parts, and preferably about 4 parts of ortho-phthalodinitrile or 1,3-diimiinoisoindoline, and a diol, such as 1,2-ethanediol (ethylene glycol), or 1,3-propanediol, in an amount of from about 3 parts to about 100 parts, and preferably about 10 parts for each part of the gallium methoxide formed at a temperature of from about 150° C. to about 220° C., and preferably at a temperature of 195° C. for a period of 30 minutes to 6 hours, and preferably about 2 hours, to provide an alkoxy-bridged gallium phthalocyanine dimer; which pigment is isolated by filtration at a temperature of about 20° C. to about 180° C., and preferably at about 120° C. to give a dark blue solid identified by elemental analysis, infrared spectroscopy, proton NMR spectroscopy and XRD.

In another embodiment, the process of the present invention comprises the reaction of a metal trihalide, like gallium trichloride, with an alcohol, like methanol, ethanol or butanol, and a base, such as ammonia, and subsequently reacting the resulting gallium alkoxide with, for example, phthalodinitrile or 1,3-diiminoisoindoline in the presence of a dialcohol (diol) which may also serve as a reaction solvent to form the alkoxy-bridged gallium phthalocyanine dimers. Embodiments of the present invention are directed to the preparation of alkoxy-bridged gallium phthalocyanine dimers, which comprise the dissolution of 1 part of a gallium trihalide, and preferably gallium trichloride in about 1 part to about 100 parts, and preferably about 10 parts of an organic solvent such as benzene, toluene, xylene or the like at a temperature of from about 0° C. to about 100° C., and preferably at a temperature of about 25° C. to form a solution of the gallium trichloride; followed by the addition of an alcohol, such as ethanol or butanol, in about 1 part to about 10 parts, and preferably about 3 parts (by weight); followed by the addition of 3 parts of an amine, such as ammonia or triethylamine or the like, at a temperature of from about 0° C. to about 60° C., and preferably at a temperature of about 25° C. to provide a gallium alkoxide solution and an ammonium halide salt byproduct, for example ammonium chloride; followed by the reaction with from about 1 part to about 10 parts, and preferably about 4 parts of ortho-phthalodinitrile or 1,3-diiminoisoindoline, and a diol, such as 1,2-ethanediol (ethylene glycol), 1,2-propanediol (propylene glycol) or 1,3-propanediol, in an amount of from about 3 parts to about 100 parts, and preferably about 10 parts, for each part of the gallium alkoxide formed at a temperature of from about 150° C. to about 220° C., and preferably at a temperature of 195° C. for a period of 30 minutes to 6 hours, and preferably about 2 hours to provide an alkoxy-bridged gallium phthalocyanine dimer; which dimer pigment is isolated by filtration at a temperature of about 20° C. to about 180° C., and preferably at about 120° C. to provide a dark blue solid identified by elemental analysis, infrared spectroscopy, proton NMR spectroscopy and XRD.

Specific preferred embodiments comprise initially preparing the trivalent metal alkoxide as indicated herein, which may then be separated from the byproduct or used in situ, followed by reaction of the metal alkoxide with phthalodinitrile or 1,3-diiminoisoindoline in a dialcohol (diol) solvent to form the alkoxy-bridged metallophthalocyanine dimer. During the aforementioned reaction, some of the dialcohol solvent is chemically incorporated into the dimer product as a bridging unit between two metallophthalocyanine units. Embodiments of the present invention are directed to the preparation of alkoxy-bridged gallium phthalocyanine dimers, which comprise the dissolution of 1 part of gallium trichloride in about 1 part to about 100 parts, and preferably about 10 parts, of an organic solvent such as benzene, toluene, xylene or the like at a temperature of from about 0° C. to about 100° C., and preferably at a temperature of about 25° C. to form a solution of the gallium trichloride; followed by the addition of 3 parts of sodium methoxide, preferably in a solution form, to provide a gallium methoxide solution and a sodium chloride byproduct at a temperature of from about 0° C. to about 100 C., and preferably at a temperature of about 20° C. to about 40° C.; followed by the reaction with from about 1 part to about 10 parts, and preferably about 4 parts of ortho-phthalodinitrile or 1,3-diiminoisoindoline, and 1,2ethanediol (ethylene glycol) in an amount of from about 3 parts to about 100 parts, and preferably about 10 parts, for each part of the gallium methoxide formed at a temperature of from about 150° C. to about 220° C., and preferably at a temperature of 195° C. for a period of 30 minutes to 6 hours, and preferably about 2 hours to provide the alkoxy-bridged gallium phthalocyanine dimer 1,2-di(oxogallium phthalocyaninyl) ethane, $C_{32}H_{16}N_8GaOCH_2CH_2OGaN_8H_{16}C_{32}$, which dimer pigment is isolated by filtration at a temperature of about 20° C. to about 180° C., and preferably at about 120° C. to provide a dark blue solid identified by elemental analysis, infrared spectroscopy, proton NMR spectroscopy and XRD.

The alkoxy-bridging unit includes components with from 2 to about 12 and preferably from 2 to about 6 carbon atoms, which are derived from the diol used in the phthalocyanine synthesis, such as 1,2-ethanediol, and the like.

The process of the present invention in embodiments comprises initially preparing the trivalent metal alkoxide as indicated herein followed by the reaction of ortho-phthalodinitrile or 1,3-diiminoisoindoline with the formed separated, or in situ trivalent metal alkoxide in a dialcohol solvent, to provide an alkoxy-bridged metallophthalocyanine dimer. During the aforementioned reaction, a portion of the dialcohol solvent is chemically incorporated into the dimer product. The resulting alkoxy-bridged metallophthalocyanine dimer, such as alkoxy-bridged galliumphthalocyanine dimers can be selected for utilization in layered photoconductive imaging members, including those that possess infrared photosensitivity, for example from about 700 to about 850 nanometers, and wherein the dimer is selected as the photogenerating pigment. The formed dimers can be selected as the photogenerating pigment or this dimer can be converted to the corresponding hydroxy metallophthalocyanine which phthalocyanine may also be selected as a photogenerating pigment. The trivalent metal alkoxide can be obtained from the reaction of the corresponding trivalent metal halide with an alkali metal alkoxide, and the alkali metal halide byproduct formed may be removed by filtration. In embodiments, the trivalent metal alkoxide can alternatively be obtained from the reaction of the corresponding trivalent metal halide with an alcohol in the presence of a base, such as ammonia, and the ammonium halide byproduct formed may be removed by filtration. Once formed, the trivalent metal alkoxide can be separated from the halide byproduct, or it may be utilized in situ in the subsequent reaction with phthalodinitrile or 1,3-diiminoisoindoline, and a diol to form the alkoxy-bridged metallophthalocyanine dimer.

The trivalent metal alkoxide can also be prepared by reacting a gallium trihalide, especially the trichloride, and an alkali metal alkoxide and thereafter reacting the resulting gallium alkoxide with, for example, phthalodinitrile or 1,3-diiminoisoindoline in the presence of a diol, plus an optional organic solvent like N-methylpyrrolidone, a halonaphthalene like 1-chloronaphthalene, quinoline, and the like to form the alkoxy-bridged galliumphthalocyanine dimer. In embodiments, the trivalent metal alkoxide selected as a reactant can be prepared by the reaction of a trivalent metal halide, like gallium trichloride, which is dissolved in an organic solvent, such as toluene, with an aliphatic alcohol like butanol, and which alcohol has from 1 to about 10 carbon atoms in the presence of a base such as ammonia, whereby there results a metal alkoxide like gallium tributoxide. The gallium butoxide formed is soluble in the organic solvent and the resulting ammonium alkali like sodium halide byproduct, such as ammonium chloride, precipitates out of solution. The ammonium halide byproduct may be removed by filtration. Thereafter, the formed gallium alkoxide is reacted with phthalodinitrile, or $DI^3$ (1,3-diiminoisoindoline) in the presence of a dialcohol, which may also serve as the reaction solvent, to form an alkoxy-bridged galliumphthalocyanine dimer. The aforementioned reaction is accomplished by heating at a temperature of from about 160° C. to about 220° C. for effective periods of time of, for example, from 30 minutes to about 1 hour.

The alkoxy-bridged metallophthalocyanine dimers, such as alkoxy-bridged gallium phthalocyanine dimers, can be selected for utilization in layered photoconductive imaging members, including those that possess infrared photosensitivity, for example from about 700 to about 850 nanometers, and wherein the dimer is selected as the photogenerating pigment. Alternatively, the alkoxy-bridged metallophthalocyanine dimer can be converted to the corresponding hydroxy metallophthalocyanine, which phthalocyanines may be selected as the photogenerating pigment.

In embodiments, the trivalent metal alkoxide can be obtained from the reaction of the corresponding metal trihalide with an alkali metal alkoxide, such as sodium ethoxide. The alkali metal halide byproduct formed can be separated from the reaction mixture by filtration, or the mixture may be utilized as is (in situ) in the subsequent reaction to form the alkoxy-bridged metallophthalocyanine dimers. In embodiments, the gallium alkoxide can be prepared by reacting a gallium trihalide, especially the trichloride, and sodium methoxide, and thereafter reacting the resulting gallium methoxide with, for example, ortho-phthalodinitrile or 1,3-diiminoisoindoline in the presence of a dialcohol (diol) which may also serve as a reaction solvent to form the alkoxy-bridged gallium phthalocyanine dimer.

Embodiments of the present invention are directed to the preparation of alkoxy-bridged metallophthalocyanine dimers, which comprise the dissolution of 1 part of a trivalent metal halide, and preferably a metal trichloride in about I part to about 100 parts, and preferably about 10 parts of an organic solvent such as benzene, toluene, xylene or the like, at a temperature of from about 0° C. to about 100° C., and preferably at a temperature of about 25° C. to form a solution of the metal trichloride; followed by the addition of 3 parts of an alkali metal alkoxide, such as sodium methoxide, sodium ethoxide, sodium propoxide or the like, preferably in a solution form to provide a trivalent metal alkoxide solution, and an alkali metal salt byproduct, for example sodium chloride, at a temperature of from about 0° C. to about 100° C., and preferably at a temperature of about 20° C. to about 40° C.; followed by the reaction with from about 1 part to about 10 parts, and preferably about 4 parts of ortho-phthalodinitrile or 1,3-diimiinoisoindoline, and a diol, such as 1,2-ethanediol (ethylene glycol), in an amount of from about 3 parts to about 100 parts, and preferably about 10 parts for each part of the metal alkoxide formed at a temperature of from about 150° C. to about 220° C., and preferably at a temperature of 195° C. for a period of 30 minutes to 6 hours, and preferably about 2 hours to provide an alkoxy-bridged metallophthalocyanine dimer; which dimer pigment is isolated by filtration at a temperature of about 20° C. to about 180° C., and preferably at about 120° C. to provide a dark blue solid. The isolated pigment is subsequently washed with an organic solvent such as dimethylformamide at a temperature of from about 20° to about 120° C., and preferably at a temperature of about 80° C., followed by washing with aqueous solvents, such as aqueous ammonium hydroxide, aqueous sodium hydroxide, or the like, cold or hot water, and possibly another organic solvent wash, to provide a pure form of the alkoxy-bridged gallium phthalocyanine dimer. Each dialcohol used for the phthalocyanine synthesis, for example 1,2-ethanediol, will produce a particular alkoxy-bridged gallium phthalocyanine dimer product like, for example, 1,2-di(oxogallium phthalocyaninyl) ethane from 1,2-ethanediol, as determined by, for example, infrared (IR) spectroscopy, nuclear magnetic resonance (NMR) spectroscopy and X-ray powder diffraction pattern (XRD).

Further, embodiments of the present invention are directed to the preparation of alkoxy-bridged gallium phthalocyanine dimers, which comprise the dissolution of 1 part of gallium trichloride in about 1 part to about 100 parts, and preferably 10 parts of toluene at a temperature of from about 0° C. to about 100° C., and preferably at a temperature of about 25° C. to form a solution of gallium chloride; followed by the addition of 3 parts of an alkali metal alkoxide, and preferably a sodium methoxide solution in methanol to form a mixture of gallium methoxide and sodium chloride byproduct, for example, at a temperature of from about 0° C. to about 100° C., and preferably at a temperature of about 20° C. to about 40° C.; followed by reaction with from about 1 part to about 10 parts, and preferably about 4 parts of ortho-phthalodinitrile, and 1,2-ethanediol (ethylene glycol) in an amount of from about 3 parts to about 100 parts, and preferably about 10 parts for each part of gallium methoxide formed at a temperature of from about 150° C. to about 220° C., and preferably at a reflux temperature of about 190° C. to about 195° C. for a period of 20 minutes to 6 hours, and preferably about 2 hours to provide the alkoxy-bridged gallium phthalocyanine dimer, 1,2-di(oxogallium phthalocyaninyl) ethane, which dimer pigment is isolated by filtration at a temperature of about 20° C. to about 180° C., and preferably at 120° C. to provide a dark blue solid. The isolated pigment is subsequently washed with an organic solvent, such as dimethylformamide, at a temperature of from about 20° C. to about 120° C., and preferably at a temperature of about 80° C., followed by optional washing with hot water, and another optional organic solvent wash to provide a pure form of the alkoxy-bridged gallium phthalocyanine dimer in a yield of about 80 percent, calculated based upon the amount of gallium chloride used. The specific alkoxy-bridged gallium phthalocyanine dimer product resulting from the synthesis with ethylene glycol is 1,2-di(oxogallium phthalocyaninyl) ethane, $C_{32}H_{16}N_8GaOCH_2CH_2OGaN_8H_{16}C_{32}$, having an XRD pattern with major peaks at Bragg angles of 6.7, 8.9, 12.8, 13.9, 15.7, 16.6, 21.2, 25.3, 25.9 and 28.3, with the highest peak at 6.7 degrees 2Θ (2theta+/−0.2°) (FIG. 3).

A preferred alkoxy-bridged gallium phthalocyanine dimer, 1,2-di(oxogallium phthalocyaninyl) ethane, $C_{32}H_{16}N_8GAOCH_2CH_2OGaN_8H_{16}C_{32}$, was characterized by elemental analysis, infrared spectroscopy, $^1H$ NMR spectroscopy, $^{13}C$ solid state CP/MAS NMR spectroscopy and X-ray powder diffraction. Elemental analysis provided values consistent with theory for the dimer structure, and in the preferred synthetic routes provided very low or minimal nonadverse levels of residual chlorine. Infrared spectroscopy of 1,2-di(oxogallium phthalocyaninyl) ethane was performed by diffuse reflectance: major peaks at 573, 611,636, 731,756, 775, 874, 897, 962, 999, 1069, 1088, 1125, 1165, 1289, 1337, 1424, 1466, 1503, 1611, 2569, 2607,2648, 2864,2950, and 3045 cm$^{-1}$ (FIG. 1). Infrared spectroscopy of the dimer did not evidence the characteristic broad hydroxyl group peak of hydroxygallium phthalocyanine at about 3,490 cm$^{-1}$, or the hydroxyl group peak expected for ethanediol (3,300 to 3,400 cm$^{-1}$). $^1H$ NMR spectroscopy (in trifluoroacetic acid, TFA-d/CDCl$_3$ solution, 1:1 v/v tetramethylsilane reference 2 milligrams of phthalocyanine per 1 milliliter solution) (FIG. 2) evidences peaks at (δ, ppm±0.01 ppm) 4.00 (4H), 8.54 (16H), and 9.62 (16H). The relative integration of 4 protons being the two CH$_2$ units from the alkoxy-bridging unit (—OCH$_2$CH$_2$—) between the two gallium phthalocyanine moieties, and the phthalocyanine dimer ring hydrogens appearing as two sets of 16 protons (NMR ratio 4: 16:16 in Table 1). The incorporated ethanediol (which forms the bridge) is liberated by hydrolysis during dissolution of the dimer in the TFA-d/CDCl$_3$ solvent. The $^{13}C$ solid state CP/MAS (cross polarization/magic angle spinning) NMR spectrum has peaks at (δ, ppm±1 ppm) 60.8 (2CH$_2$), 124.0 (16CH), 129.1 (16CH), 135.5 (16C), and 152.6 (16C). All the NMR data are consistent with the formula $C_{32}H_{16}N_8GaOCH_2CH_2OGaN_8H_{16}C_{32}$ for 1,2-di-(oxogallium phthalocyaninyl) ethane. A summary of the expected NMR, IR and XRD results for $C_{32}H_{16}N_8GaOCH_2OGaN_8H_{16}C_{32}$ [(PcGaOCH$_2$)$_2$], compared to other gallium phthalocyanine structures, and the actual measurements are provided in Table 1.

TABLE 1

| STRUCTURE | EXPECTED RESULT | | |
| --- | --- | --- | --- |
| | NMR PROTON RATIO | IR PEAK | XRD |
| HOGaPc | 0:8:8 | Ga—OH | Known |
| HOGaPc + HOCH$_2$CH$_2$OH | X:8:8 | Ga—OH | Known |
| PcGaOCH$_2$CH$_2$OH | 4:8:8 | CH2—OH | New |
| (PcGaOCH$_2$)$_2$ (Dimer) | 4:16:16 | No OH | New |
| Actual Measurement | 4:16:16 | No OH | New |

A review of Examples I to IX illustrate that despite some variations in the preferred synthetic procedure and the form of gallium source used, when the phthalocyanine synthesis is performed in ethylene glycol, the same polymorph of 1,2-di(oxogallium phthalocyaninyl) ethane is obtained (with variations in the degree of crystallinity which result in changes in peak sharpness and relative intensities).

Advantages associated with the the present invention include a single step synthesis of new phthalocyanine compounds from inexpensive starting materials, such as gallium trichloride, which phthalocyanines may be used as photogenerators having very low levels of chlorine, in parts per million for example, retained and thus possess excellent dark decay and cycling properties.

In embodiments, the layered photoresponsive imaging members are comprised of a supporting substrate, a charge transport layer, especially an aryl amine hole transport layer, and situated therebetween a photogenerator layer comprised of an alkoxy-bridged metallophthalocyanine dimer, the corresponding hydroxy metallophthalocyanine photogenerating pigment, or mixtures thereof, and preferably 1,2-di(oxogallium phthalocyaninyl) ethane and hydroxygallium phthalocyanine Type V. Another embodiment of the present invention is directed to positively charged layered photoresponsive imaging members comprised of a supporting substrate, a charge transport layer, especially an aryl amine hole transport layer, and as a top overcoating layer an alkoxy-bridged metallophthalocyanine dimer, or the corresponding hydroxy metallophthalocyanines obtained with the processes of the present invention. Moreover, there is provided in accordance with the present invention an improved negatively charged photoresponsive imaging member comprised of a supporting substrate, a thin adhesive layer, an alkoxy-bridged metallophthalocyanine dimer, or the corresponding hydroxy metallophthalocyanines photogenerator layer obtained by the processes of the present invention dispersed in a polymeric resinous binder, such as poly(vinyl butyral), and as a top layer aryl amine hole transporting molecules dispersed in a polymeric resinous binder such as polycarbonate.

The photoresponsive imaging members of the present invention can be prepared by a number of known methods, the process parameters and the order of coating of the layers being dependent on the member desired. The imaging members suitable for positive charging can be prepared by reversing the order of deposition of photogenerator and hole transport layers. The photogenerating and charge transport layers of the imaging members can be coated as solutions or dispersions onto selective substrates by the use of a spray coater, dip coater, extrusion coater, roller coater, wire-bar coater, slot coater, doctor blade coater, gravure coater, and the like, and dried at from 40° C. to about 200° C. for from 10 minutes to several hours under stationary conditions or in an air flow. The coating is accomplished to provide a final coating thickness of from 0.01 to about 30 microns after it has dried. The fabrication conditions for a given layer can be tailored to achieve optimum performance and cost in the final device.

Imaging members of the present invention are useful in various electrostatographic imaging and printing systems, particularly those conventionally known as xerographic processes. Specifically, the imaging members of the present invention are useful in xerographic imaging processes wherein the photogenerating pigment absorbs light of a wavelength of from about 650 to about 900 nanometers, and preferably from about 700 to about 850 nanometers. In these known processes, electrostatic latent images are initially formed on the imaging member followed by development, and thereafter transferring the image to a suitable substrate. Imaging members employing the photogenerator pigments of the present invention exhibit high photosensitivities, generally with $E_{1/2}$ of about 2.0 ergs/cm$^2$ or less, even when exposed to monochromatic radiation of about 700 to 800 nanometers.

Moreover, the imaging members of the present invention can be selected for electronic printing processes with gallium arsenide light emitting diode (LED) arrays which typically function at wavelengths of from 660 to about 830 nanometers.

One negatively charged photoresponsive imaging member of the present invention is comprised, in the order indicated, of a supporting substrate, an adhesive layer comprised, for example, of a polyester 49,000 available from Goodyear Chemical, a photogenerator layer comprised of 1,2-di(oxogallium phthalocyaninyl) ethane or 1,3-di(oxogallium phthalocyaninyl) propane obtained with the process of the present invention, optionally dispersed in an inactive polymer binder, and a hole transport layer thereover comprised of N,N'-diphenyl-N,N'-bis(3-methyl phenyl)-1,1'-biphenyl-4,4'-diamine dispersed in a polycarbonate binder, and a positively charged photoresponsive imaging member comprised of a substrate, thereover a charge transport layer comprised of N,N'-diphenyl-N,N'-bis(3-methyl phenyl)-1,1'-biphenyl-4,4'-diamine dispersed in a polycarbonate binder, and a top photogenerator layer comprised of the aforementioned alkoxy-bridged metallophthalocyanines dimer obtained with the process of the present invention optionally dispersed in an inactive polymer binder.

Substrate layers selected for the imaging members of the present invention can be opaque or substantially transparent, and may comprise any suitable material having the requisite mechanical properties. Thus, the substrate may comprise a layer of insulating material including inorganic or organic polymeric materials, such as MYLAR® a commercially available polymer, MYLAR® containing titanium, a layer of an organic or inorganic material having a semiconductive surface layer such as indium tin oxide, or aluminum arranged thereon, or a conductive material inclusive of aluminum, chromium, nickel, brass or the like. The substrate may be flexible, seamless, or rigid ,and many have a number of many different configurations, such as for example a plate, a cylindrical drum, a scroll, an endless flexible belt and the like. In one embodiment, the substrate is in the form of a seamless flexible belt. In some situations, it may be desirable to coat on the back of the substrate, particularly when the substrate is a flexible organic polymeric material, an anticurl layer, such as for example polycarbonate materials commercially available as MAKROLON®.

The thickness of the substrate layer depends on many factors, including economical considerations, thus this layer may be of substantial thickness, for example over 3,000 microns, or of minimum thickness. In embodiment, the thickness of this layer is from about 75 microns to about 300 microns.

With further regard to the imaging members, the photogenerator layer is comprised of an alkoxy-bridged metallophthalocyanine dimer, such as 1,2-di(oxogallium phthalocyaninyl) ethane, obtained with the processes of the present invention dispersed in polymer binders. Generally, the thickness of the photogenerator layer depends on a number of factors, including the thicknesses of the other layers and the amount of photogenerator material contained in this layer. Accordingly, this layer can be of a thickness of from about 0.05 micron to about 10 microns when the phthalocyanine photogenerator composition is present in an amount of from about 5 percent to about 100 percent by volume. In one embodiment, this layer is of a thickness of from about 0.25 micron to about 1 micron when the photogenerator composition is present in this layer in an amount of 30 to 75 percent by volume. The maximum thickness of this layer in an embodiment is dependent primarily upon factors, such as photosensitivity, electrical properties and mechanical considerations. The photogenerator layer can be fabricated by coating a dispersion of the phthalocyanine obtained with the processes of the present invention in a suitable solvent with or without an optional polymer binder material. The dispersion can be prepared by mixing and/or milling the phthalocyanine component in equipment such as paint shakers, ball mills, sand mills and attritors. Common grinding media such as glass beads, steel balls or ceramic beads may be used in this equipment. The binder resin may be selected from a number of known polymers such as poly(vinyl butyral), poly(vinyl carbazole), polyesters, polycarbonates, poly(vinyl chloride), polyacrylates and methacrylates, copolymers of vinyl chloride and vinyl acetate, phenoxy resins, polyurethanes, poly(vinyl alcohol), polyacrylonitrile, polystyrene, and the like. In embodiments of the present invention, it is desirable to select a coating solvent that does not disturb or adversely affect the other previously coated layers of the device. Examples of solvents that can be selected for use as coating solvents for the photogenerator layer are ketones, alcohols, aromatic hydrocarbons, halogenated aliphatic hydrocarbons, ethers, amines, amides, esters, and the like. Specific examples are cyclohexanone, acetone, methyl ethyl ketone, methanol, ethanol, butanol, amyl alcohol, toluene, xylene, chlorobenzene, carbon tetrachloride, chloroform, methylene chloride, trichloroethylene, tetrahydrofuran, dioxane, diethyl ether, dimethylformamide, dimethylacetamide, butyl acetate, ethyl acetate, methoxyethyl acetate, and the like.

The coating of the photogenerator layer in embodiments of the present invention can be accomplished with spray, dip or wire-bar methods such that the final dry thickness of the photogenerator layer is from 0.01 to 30 microns and preferably from 0.1 to 15 microns after being dried at 40° C. to 150° C. for 5 to 90 minutes.

Illustrative examples of polymeric binder materials that can be selected for the photogenerator pigment include those polymers as disclosed in U.S. Pat. No. 3,121,006, the disclosure of which is totally incorporated herein by reference. The binder resin may be selected from a wide number of polymers such as polyesters, poly(vinyl butyral), poly(vinyl carbazole), polycarbonates, poly(vinyl chloride), polyacrylates and methacrylates, phenoxy resins, polyurethanes, poly(vinyl alcohol), polyacrylonitrile, polystyrene, copolymers and block copolymers of selected monomers such as styrene and vinylpyridine, and the like. The solvents used to dissolve these binders depend upon the particular resin. The binder may be used in from about 0.5 part to about 10 parts for each part of dimer photogenerator pigment which is selected.

As adhesives usually in contact with the supporting substrate, there can be selected various known substances inclusive of polyesters, polyamides, poly(vinyl butyral), poly(vinyl alcohol), polyurethane and polyacrylonitrile. This layer is of a thickness of from about 0.001 micron to about 1 micron. Optionally, this layer may contain conductive and nonconductive particles, such as zinc oxide, titanium dioxide, silicon nitride, carbon black, and the like, to provide, for example, in embodiments of the present invention desirable electrical and optical properties.

Aryl amines selected for the hole transporting layer, which generally is of a thickness of from about 5 microns to about 75 microns, and preferably of a thickness of from about 10 microns to about 40 microns, include molecules of the following formula

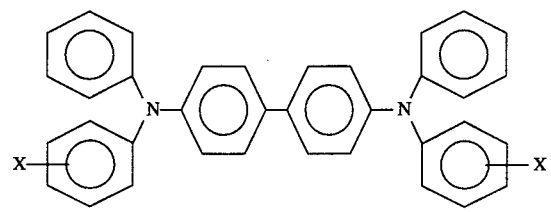

dispersed in a highly insulating and transparent polymer binder, wherein X is an alkyl group or a halogen, especially those substituents selected from the group consisting of Cl and $CH_3$.

Examples of specific aryl amines are N,N'-diphenyl-N,N'-bis(alkylphenyl)-1,1-biphenyl-4,4'-diamine wherein alkyl is selected from the group consisting of methyl, ethyl, propyl, butyl, hexyl, and the like; and N,N'-diphenyl-N,N'-bis(halophenyl)- 1,1'-biphenyl-4,4'-diamine wherein the halo substituent is preferably a chloro substituent. Other known charge transport layer molecules can be selected, reference for example U.S. Pat. Nos. 4,921,773 and 4,464,450, the disclosures of which are totally incorporated herein by reference.

Examples of the highly insulating and transparent polymer binder material for the transport layers include materials such as those described in U.S. Pat. No. 3,121,006, the disclosure of which is totally incorporated herein by reference. Specific examples of polymer binder materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binders are comprised of polycarbonate resins having a molecular weight of from about 20,000 to about 100,000 with a molecular weight of from about 50,000 to about 100,000 being particularly preferred. Generally, the transport layer contains from about 10 to about 75 percent by weight of the charge transport material, and preferably from about 35 percent to about 50 percent of this material.

Also, included within the scope of the present invention are methods of imaging and printing with the photoresponsive devices illustrated herein. These methods generally involve the formation of an electrostatic latent image on the imaging member, followed by developing the image with a toner composition, reference U.S. Pat. Nos. 4,560,635; 4,298,697 and 4,338,390, the disclosures of which are totally incorporated herein by reference, subsequently transferring the image to a suitable substrate, and permanently affixing the image thereto. In those environments wherein the device is to be used in a printing mode, the imaging method involves the same steps with the exception that the exposure step can be accomplished with a laser device or image bar.

BRIEF DESCRIPTION OF THE DRAWINGS

For a better understanding of the present invention and further features thereof, reference is made to the following characterization data collected for the various preferred embodiments wherein.

The following Examples are provided. These Examples are intended to be illustrative only. The invention is not intended to be limited to the materials, conditions, or process parameters recited herein.

EXAMPLE I

Figure 1:
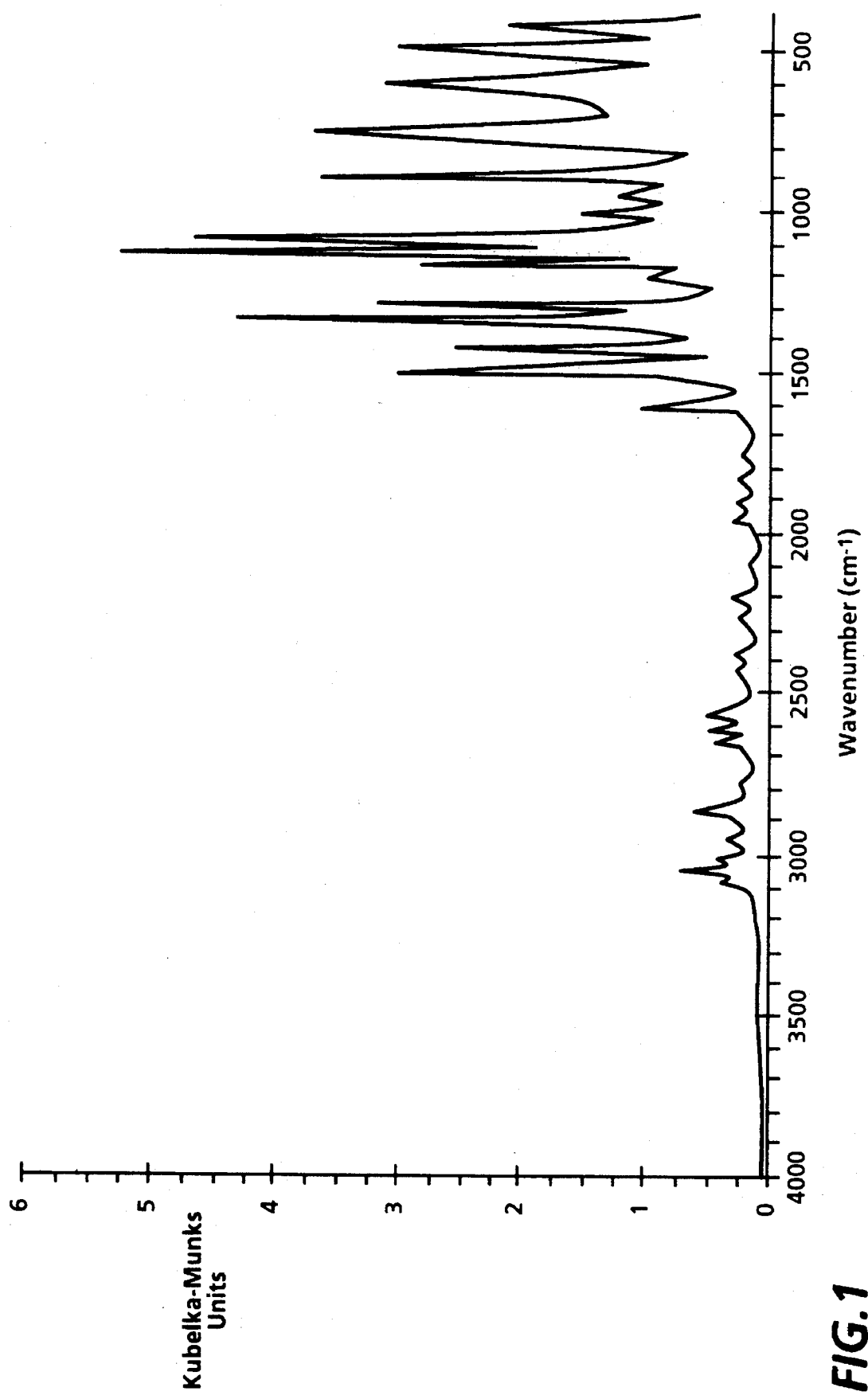
FIG. 1 represents an infrared plot of the alkoxy-bridged phthalocyanine dimer prepared as described in Example I, which has the formula $C_{32}H_{16}N_8GaOCH_2CH_2OGaN_8H_{16}C_{32}$.
Figure 2:
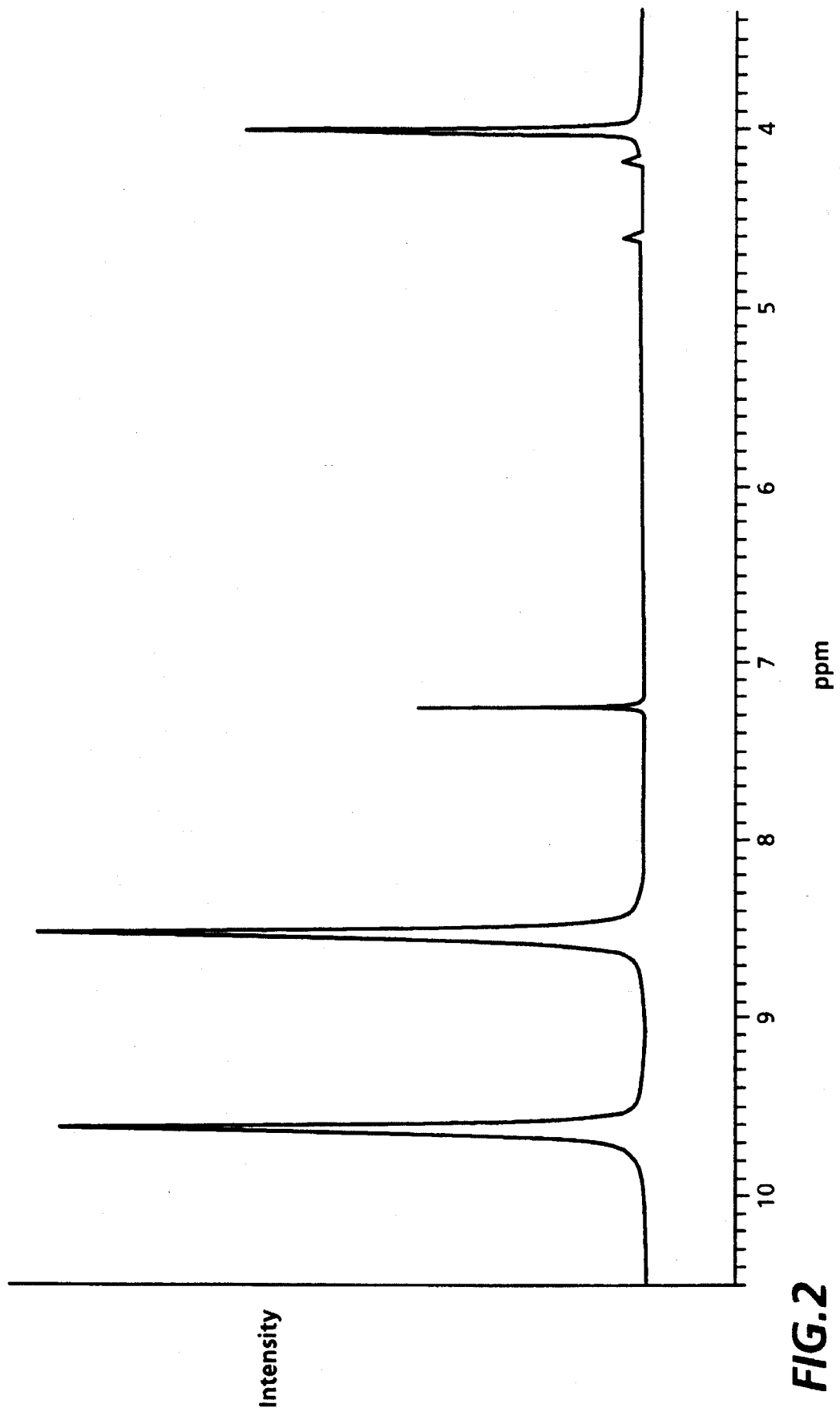
FIG. 2 represents a plot of $^1H$ NMR spectroscopy (in TFA-d/$CDCl_3$ solution) of the alkoxy-bridged phthalocyanine dimer prepared as described in Example I.
Figure 3:
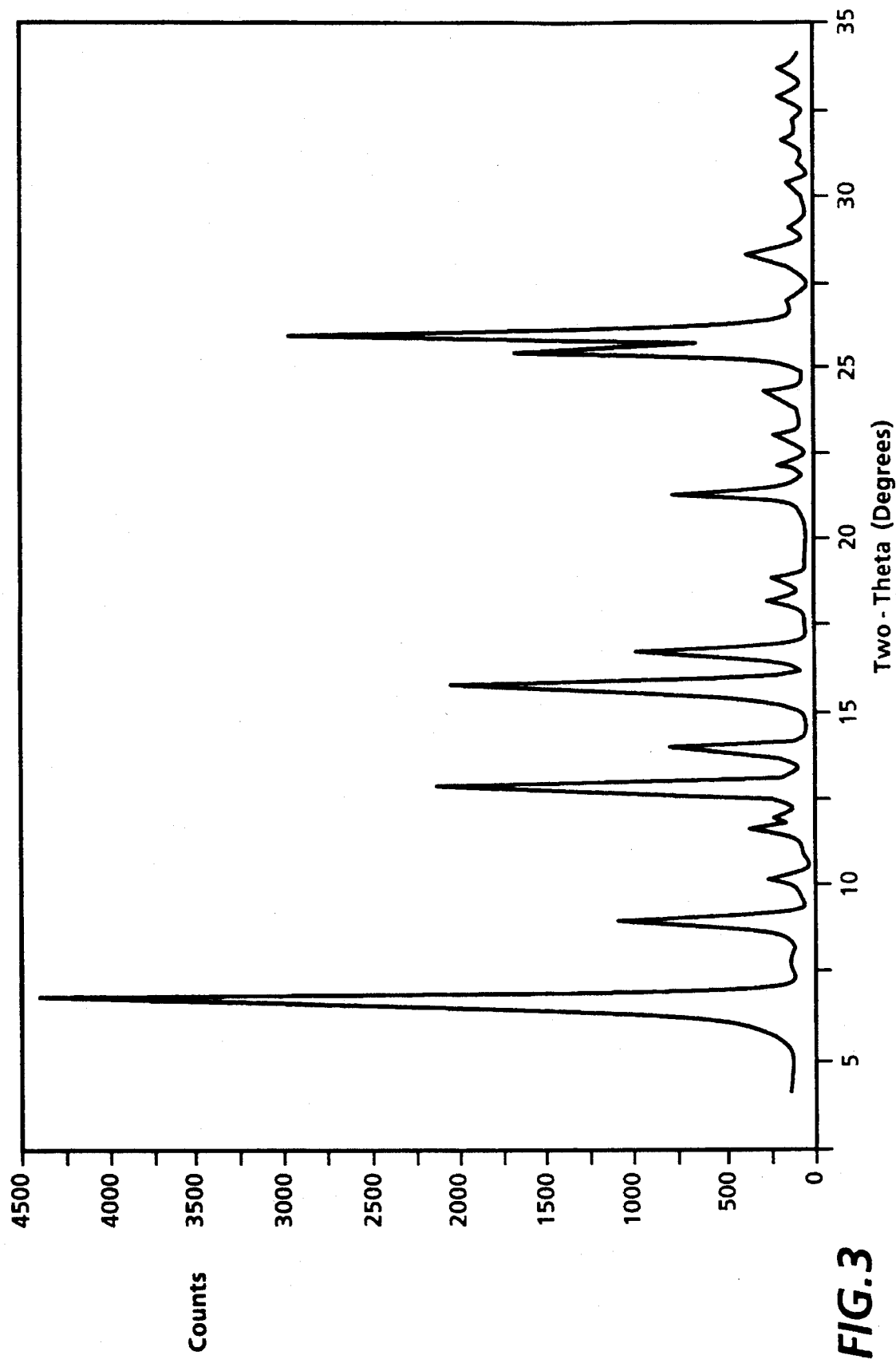
FIG. 3 represents an X-ray powder diffraction trace for the alkoxy-bridged gallium phthalocyanine dimer (Type I polymorph) prepared as described in Example I.

Alkoxy-bridged Gallium Phthalocyanine Dimer Synthesis Using Gallium Methoxide Obtained From Gallium Chloride and Sodium Methoxide In Situ:

To a 1 liter round bottomed flask were added 25 grams of $GaCl_3$ and 300 milliliters of toluene and the mixture was stirred for 10 minutes to form a solution. Then 98 milliliters of a 25 weight percent sodium methoxide solution (in methanol) were added while cooling the flask with an ice bath to retain the contents below 40° C. Thereafter, 250 milliliters of ethylene glycol and 72.8 grams of o-phthalodinitrile were added. The methanol and toluene were distilled off over 30 minutes while heating from 70° C. to 135° C., and then the phthalocyanine synthesis was performed by heating at 195° C. for 2 hours, followed by cooling. The alkoxy-bridged gallium phthalocyanine dimer was isolated by filtration at 120° C. The product was then washed with 400 milliliters of DMF at 100° C. for 1 hour and filtered. The product was then washed with 400 milliliters of deionized water at 80° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated in 80 percent yield. The pigment was characterized by elemental analysis, infrared spectroscopy, $^1H$ NMR spectroscopy, $^{13}C$ solid state CP/MAS (cross polarization/magic angle spinning) NMR spectroscopy and X-ray powder diffraction. Elemental analysis showed the presence of 0.05 percent chlorine. Infrared spectroscopy: major peaks at 573, 611,636, 731, 756, 775,874, 897,962,999, 1069, 1088, 1125, 1165, 1289, 1337, 1424, 1466, 1503, 1611,2569, 2607, 2648, 2864, 2950,and 3045 $cm^{-1}$ (FIG. 1); $^1H$ NMR spectroscopy (TFA-d/CDCl$_3$ solution, 1:1 v/v, tetramethylsilane reference): peaks at ($\delta$, ppm±0.01 ppm) 4.00 (4H), 8.54 (16H), and 9.62 (16H) (FIG. 2); $^{13}C$ solid state CP/MAS NMR spectroscopy: peaks at ($\delta$, ppm±1 ppm): 60.2 (2CH$_2$), 124.2 (16CH), 129.1 (16CH), 135.1 (16C), and 152.8 (16C); X-ray powder diffraction pattern: peaks at Bragg angles (2$\Theta$±0.2°) of 6.7, 8.9, 12.8, 13.9, 15.7, 16.6, 21.2, 25.3, 25.9, and 28.3, with the highest peak at 6.7 degrees 2$\Theta$ (FIG. 3).

EXAMPLE II

Alkoxy-bridged Gallium Phthalocyanine Dimer Synthesis Using Gallium Ethoxide Obtained From Gallium Chloride and Sodium Ethoxide Ex Situ:

To a 500 milliliter round bottomed flask were added 25 grams of $GaCl_3$ and 300 milliliters of toluene, and the mixture was stirred for 10 minutes to form a solution. Then, 160 milliliters of a 21 weight percent sodium ethoxide solution (in ethanol) were added while cooling the flask with an ice bath to retain the contents below 60° C. The mixture was stirred for 15 minutes and then filtered to remove the sodium chloride byproduct. The gallium ethoxide solution resulting was then transferred to a 1 liter round bottomed flask and 250 milliliters of ethylene glycol and 72.8 grams of o-phthalodinitrile were added. The ethanol and toluene were distilled off over 30 minutes while heating from 90° C. to 135° C., and then the reaction mixture was heated while the phthalocyanine synthesis was performed at 195° C. for 4.5 hours, followed by cooling. The alkoxy-bridged gallium phthalocyanine dimer was isolated by filtration at 120° C. The product was then washed with 400 milliliters of DMF at 100° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated in 62 percent yield. The pigment (dimer) was characterized by elemental analysis, infrared spectroscopy, $^1H$ NMR spectroscopy and X-ray powder diffraction. Elemental analysis showed the presence of only 0.05 percent chlorine. Infrared spectroscopy: major peaks at 573, 611,636, 731, 756, 775, 874, 897,962,999, 1069, 1088, 1125, 1165, 1289, 1337, 1424, 1466, 1503, 1611, 2569, 2607, 2648, 2864, 2950, and 3045 $cm^{-1}$ (identical to FIG. 1); $^1H$ NMR spectroscopy (TFA-d/CDCl$_3$ solution, 1:1 v/v, tetramethylsilane reference): peaks at ($\delta$, ppm ±0.01 ppm) 4.00 (4H), 8.54 (16H), and 9.62 (16H) (identical to FIG. 2); X-ray powder diffraction pattern: peaks at Bragg angles (2$\Theta$±0.2°) of 6.7, 8.9, 12.8, 13.9, 15.7, 16.6, 21.2, 25.3, 25.9, and 28.3, with the highest peak at 6.7 degrees 2$\Theta$ (identical to FIG. 3).

EXAMPLE III

Alkoxy-bridged Gallium Phthalocyanine Dimer Synthesis Using Gallium Methoxide Obtained From Gallium Chloride and Sodium Methoxide In Situ:

To a 1 liter round bottomed flask were added 25 grams of $GaCl_3$ and 300 milliliters of toluene, and the mixture was stirred for 10 minutes to form a solution. Then, 98 milliliters of a 25 weight percent sodium methoxide solution (in methanol) were added while cooling the flask with an ice bath to keep the contents below 40° C. Then, 250 milliliters of ethylene glycol and 72.8 grams of o-phthalodinitrile were added. The methanol and toluene were distilled off over 30 minutes while heating from 70° C. to 135° C., and then the phthalocyanine synthesis was performed by heating at 195° C. for 4.5 hours, followed by cooling. The alkoxy-bridged gallium phthalocyanine dimer was isolated by filtration at 120° C. The product was then washed with 400 milliliters of DMF at 100° C. for 1 hour and filtered. The product was then washed three times with 600 milliliters of an aqueous 10 percent NaOH solution at 25° C. for 0.5 hour, followed by several water washes, each with a filtration. The product was then washed with 600 milliliters of methanol at 25° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated in 77 percent yield. The dimer pigment was characterized by elemental analysis, infrared spectroscopy, $^1H$ NMR spectroscopy and X-ray powder diffraction. Elemental analysis showed the presence of only 0.10 percent chlorine. Infrared spectroscopy: major peaks at 573, 611, 636, 731, 756, 775, 874, 897, 962,999, 1069, 1088, 1125, 1165, 1289, 1337, 1424, 1466, 1503, 1611, 2569, 2607, 2648, 2864, 2950, and 3045 $cm^{-1}$ (identical to FIG. 1); $^1H$ NMR spectroscopy (TFA-d/CDCl$_3$ solution, 1:1 v/v, tetramethylsilane reference): peaks at ($\delta$, ppm ±0.01 ppm) 4.00 (4H), 8.54 (16H), and 9.62 (16H) (identical to FIG. 2); X-ray powder diffraction pattern: peaks at Bragg angles (2$\Theta$±0.2°) of 6.7, 8.9, 12.8, 13.9, 15.7, 16.6, 21.2, 25.3, 25.9, and 28.3, with the highest peak at 6.7 degrees 2$\Theta$ (identical to FIG. 3).

EXAMPLE IV

Alkoxy-bridged Gallium Phthalocyanine Dimer Synthesis Using Gallium Methoxide Obtained From Gallium Chloride and Sodium Methoxide In Situ:

To a 1 liter round bottomed flask were added 25 grams of $GaCl_3$ and 300 milliliters of toluene, and the mixture was stirred for 10 minutes to form a solution. Subsequently, 98 milliliters of a 25 weight percent sodium methoxide solution (:in methanol) were added while cooling the flask with an ice bath to keep the contents below 40° C. Then, 250 milliliters of ethylene glycol and 83.6 grams of 1,3-diiminoisoindoline were added. The methanol and toluene were distilled off over 30 minutes while heating from 70° C. to 135° C., and then the phthalocyanine synthesis was performed by heating at 195° C. for 2 hours, followed by cooling. The alkoxy-bridged gallium phthalocyanine dimer was isolated by filtration at 120° C. The product was then washed with 400 milliliters of DMF at 100° C. for 1 hour and filtered. The product was then washed with 400 milliliters of deionized water at 80° C. for 1 hour and filtered. The dimer product was then washed with 400 milliliters methanol of at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated in 75 percent yield. The pigment was characterized by elemental analysis, infrared spectroscopy, 1H NMR spectroscopy and X-ray powder diffraction. Elemental analysis showed the presence of 0.05 percent chlorine. Infrared spectroscopy: major peaks at 573, 611,636, 731, 756, 775, 874, 897, 962, 999, 1069, 1088, 1125, 1165, 1289, 1337, 1424, 1466, 1503, 1611, 2569, 2607, 2648, 2864, 2950, and 3045 $cm^{-1}$ (identical to FIG. 1); $^1H$ NMR spectroscopy (TFA-d/$CDCl_3$ solution, 1:1 v/v, tetramethylsilane reference): peaks at ($\delta$, ppm $\pm$0.01 ppm) 4.00 (4H), 8.54 (16H), and 9.62 (16H) (identical to FIG. 2); X-ray powder diffraction pattern: peaks at Bragg angles (2$\Theta$$\pm$0.2°) of 6.7, 8.9, 12.8, 13.9, 15.7, 16.6, 21.2, 25.3, 25.9, and 28.3, with the highest peak at 6.7 degrees 2$\Theta$ (identical to FIG. 3).

EXAMPLE V

Alkoxy-bridged Gallium Phthalocyanine Dimer Synthesis Using Gallium Butoxide:

To a 1 liter round bottomed flask were added 41.1 grams of $Ga(OBu)_3$ purchased from APL Engineering Materials, and 250 milliliters of ethylene glycol and 72.8 grams of o-phthalodinitrile. The butanol distillate was collected in a Dean Stark trap while the phthalocyanine synthesis was performed at 195° C. for 4.5 hours. The alkoxy-bridged gallium phthalocyanine dimer was isolated by filtration at 120° C. The product was then washed with 400 milliliters of DMF at 100° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated in 78 percent yield. The aforementioned product dimer pigment was characterized by elemental analysis, infrared spectroscopy and X-ray powder diffraction. Elemental analysis showed the presence of only 0.02 percent chlorine. Infrared spectroscopy: major peaks at 573, 611,636, 731, 756, 775, 874, 897,962,999, 1069, 1088, 1125, 1165, 1289, 1337, 1424, 1466, 1503, 1611, 2569, 2607, 2648, 2864, 2950, and 3045 $cm^{-1}$ (identical to FIG. 1); $^1H$ NMR spectroscopy (TFA-d/$CDCl_3$ solution, 1:1 v/v, tetramethylsilane reference): peaks at ($\delta$, ppm $\pm$0.01 ppm) 4.00 (4H), 8.54 (16H), and 9.62 (16H) (identical to FIG. 2); X-ray powder diffraction pattern: peaks at Bragg angles (2$\Theta$$\pm$0.2°) of 6.7, 8.9, 12.8, 13.9, 15.7, 16.6, 21.2, 25.3, 25.9, and 28.3, with the highest peak at 6.7 degrees 2$\Theta$ (identical to FIG. 3).

EXAMPLE VI

Alkoxy-bridged Gallium Phthalocyanine Dimer Synthesis Using Gallium Acetylacetonate:

To a 1 liter round bottomed flask were added 53.4 grams of $Ga(acac)_3$ of Example V, and 250 milliliters of ethylene glycol and 74.6 grams of o-phthalodinitrile. The acetylacetonate (2,4-pentanedione) distillate was collected in a Dean Stark trap while the phthalocyanine synthesis was performed at 195° C. for 2.5 hours. The alkoxy-bridged gallium phthalocyanine dimer was isolated by filtration at 120° C. The product was then washed with 400 milliliters of DMF at 100° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated in 75 percent yield. This dimer product pigment was characterized by elemental analysis, infrared spectroscopy, $^1H$ NMR spectroscopy and X-ray powder diffraction. Elemental analysis showed the presence of 0.02 percent chlorine. Infrared spectroscopy: major peaks at 573, 611, 636, 731,756, 775, 874, 897, 962, 999, 1069, 1088, 1125, 1165, 1289, 1337, 1424, 1466, 1503, 1611, 2569, 2607, 2648, 2864, 2950, and 3045 $cm^{-1}$ (identical to FIG. 1); $^1H$ NMR spectroscopy (TFA-d/$CDCl_3$ solution, 1:1 v/v, tetramethylsilane reference): peaks at ($\delta$, ppm $\pm$0.01 ppm)4.00 (4H), 8.54 (16H), and 9.62 (16H) (identical to FIG. 2); X-ray powder diffraction pattern: peaks at Bragg angles (2$\Theta$$\pm$0.220) of 6.7, 8.9, 12.8, 13.9, 15.7, 16.6, 21.2, 25.3, 25.9, and 28.3, with the highest peak at 6.7 degrees 2$\Theta$ (identical to FIG. 3).

EXAMPLE VII

Alkoxy-bridged Gallium Phthalocyanine Dimer Synthesis Using Gallium Acetate:

To a 1 liter round bottomed flask were added 25.0 grams of $Ga(OAc)_3$ of Example V, and 190 milliliters of ethylene glycol and 51.9 grams of o-phthalodinitrile. The acetic acid distillate was collected in a Dean Stark trap while the phthalocyanine synthesis was performed at 195° C. for 5 hours. The alkoxy-bridged gallium phthalocyanine dimer was isolated by filtration at 120° C. The product was then washed with 400 milliliters of DMF at 100° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated in 51 percent yield. The dimer product pigment was characterized by elemental analysis, infrared spectroscopy, $^1H$ NMR spectroscopy and X-ray powder diffraction. Elemental analysis showed the presence of 0.09 percent chlorine. Infrared spectroscopy: major peaks at 573, 611,636, 731, 756, 775, 874, 897, 962,999, 1069, 1088, 1125, 1165, 1289, 1337, 1424, 1466, 1503, 1611, 2569, 2607, 2648, 2864, 2950, and 3045 $cm^{-1}$ (identical to FIG. 1); $^1H$ NMR spectroscopy (TFA-d/$CDCl_3$ solution, 1:1 v/v, tetramethylsilane reference): peaks at ($\delta$, ppm $\pm$0.01 ppm) 4.00 (4H), 8.54 (16H), and 9.62 (16H) (identical to FIG. 2); X-ray powder diffraction pattern: peaks at Bragg angles (2$\Theta$$\pm$0.220) of 6.7, 8.9, 12.8, 13.9, 15.7, 16.6, 21.2, 25.3, 25.9, and 28.3, with the highest peak at 6.7 degrees 2Θ (identical to FIG. 3).

EXAMPLE VIII

Alkoxy-bridged Gallium Phthalocyanine Dimer Synthesis Using Gallium Butoxide Obtained From Gallium Chloride and Butanol With Ammonia Ex Situ:

To a 500 milliliter round bottomed flask was were added 25 grams of $GaCl_3$ and 200 milliliters of toluene, and the mixture was stirred for 10 minutes to form a solution. Then, 70 milliliters of n-butanol were added, followed by 7.7 grams of ammonia bubbled into the solution while cooling the flask with an ice bath to keep the contents below 30° C. The mixture was stirred for 15 minutes and then filtered to remove the ammonium chloride byproduct. The filtercake was rinsed with 100 milliliters of toluene and then the gallium butoxide solution was transferred to a 1 liter round bottomed flask. Then, 250 milliliters of ethylene glycol and 72.8 grams of o-phthalodinitrile were added. The butanol and toluene were distilled off over 30 minutes while heating from 110° C. to 135° C., and then the phthalocyanine synthesis was performed at 195° C. for 4.5 hours. The alkoxy-bridged gallium phthalocyanine dimer was isolated by filtration at 120° C. The product was then washed with 400 milliliters of DMF at 100° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated in 40 percent yield. The product pigment was characterized by elemental analysis, infrared spectroscopy, $^1H$ NMR spectroscopy and X-ray powder diffraction. Elemental analysis showed the presence of 0.51 percent chlorine. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 $cm^{-1}$ (identical to FIG. 1); $^1H$ NMR spectroscopy (TFA-d/CDCl$_3$ solution, 1:1 v/v, tetramethylsilane reference): peaks at (δ, ppm±0.01 ppm) 4.00 (4H), 8.54 (16H), and 9.62 (16H) (identical to FIG. 2); X-ray powder diffraction pattern: peaks at Bragg angles (2Θ±0.2°) of 6.7, 8.9, 12.8, 13.9, 15.7, 16.6, 21.2, 25.3, 25.9, and 28.3, with the highest peak at 6.7 degrees 2Θ (identical to FIG. 3).

EXAMPLE IX

Synthesis of Alkoxy-bridged Gallium Phthalocyanine Dimer From Hydroxycallium Phthalocyanine:

To a 500 milliliter round bottomed flask were added 6.0 grams of hydroxygallium phthalocyanine and 200 milliliters of ethylene glycol (1,2-ethanediol). The mixture was stirred while heating at 120° C. for 5 hours. The alkoxy-bridged gallium phthalocyanine dimer was isolated by filtration and then twice washed with 200 milliliters of methanol. The product was dried at 60° C. under vacuum for 18 hours. The alkoxy-bridged gallium phthalocyanine pigment dimer, 1,2-di(oxogallium phthalocyaninyl) ethane, was isolated in 90 percent yield. The pigment was characterized by elemental analysis, infrared spectroscopy, $^1H$ NMR spectroscopy, $^{13}C$ solid state CP/MAS (cross polarization/magic angle spinning) NMR spectroscopy and X-ray powder diffraction. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 $cm^{-1}$ (identical to FIG. 1); $^1H$ NMR spectroscopy (TFA-d/CDCl$_3$ solution, 1:1 v/v, tetramethylsilane reference): peaks at (δ, ppm±0.01 ppm) 4.00 (4H), 8.54 (16H), and 9.62 (16H) (identical to FIG. 2); $^{13}C$ solid state CP/MAS NMR spectroscopy: peaks at (δ, ppm ±1 ppm): 60.2 (2CH$_2$), 124.2 (16CH), 129.1 (16CH), 135.1 (16C), and 152.8 (16C); X-ray powder diffraction pattern: peaks at Bragg angles (2Θ±0.220) of 6.7, 8.9, 12.8, 13.9, 15.7, 16.6, 21.2, 25.3, 25.9, and 28.3, with the highest peak at 6.7 degrees 2Θ (identical to FIG. 3).

Other embodiments and modifications of the present invention may occur to those skilled in the art subsequent to a review of the information presented herein; these embodiments and modifications, as well as equivalents thereof, are also included within the scope of this invention.

What is claimed is:

1. Alkoxy-bridged metallophthalocyanine dimers of the formula $C_{32}H_{16}N_8MOROMN_8H_{16}C_{32}$, or of the formula

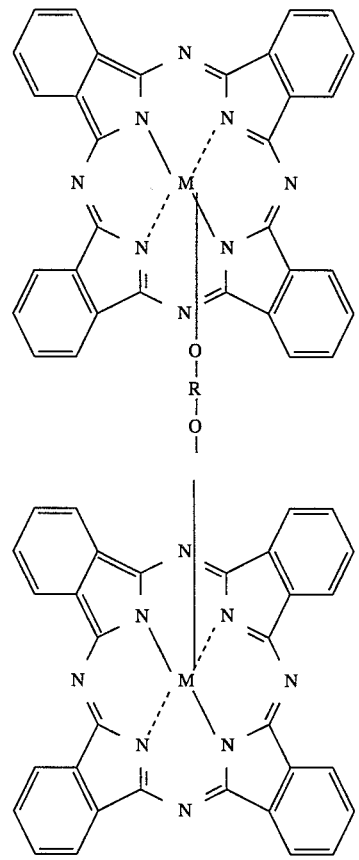

wherein M is a metal, and R is an alkyl or an alkyl ether.

2. Alkoxy-bridged metallophthalocyanine dimers in accordance with claim 1 wherein M is a trivalent metal of aluminum, gallium or indium, or a trivalent transition metal of Fe(III), Cr(III), Co(III), Mn(III), Ni(III), or V(III), and R is selected from the group consisting of:

—(CH$_2$)$_n$— wherein n is from about 2 to about 12

—CH$_2$—CH— wherein n is from about 0 to 4
      |
   (CH$_2$)$_n$
      |
   CH$_3$ -continued

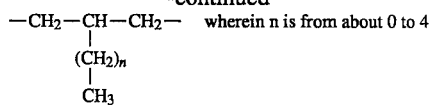  wherein n is from about 0 to 4

—[(CH₂)ₘ—O—(CH₂)ₘ]ₙ—  wherein n is from about 1 to about 4, and m is from about 2 to about 4

—[CH(CH₃)CH₂—O—CH₂(CH₃)CH]ₙ—  wherein n is from about 1 to about 3.

wherein n is from about 1 to about 3.

3. Alkoxy-bridged metallophthalocyanine dimers in accordance with claim 1 wherein M is aluminum, and R is an alkyl group with from 1 to about 25 carbon atoms.

4. Alkoxy-bridged metallophthalocyanine dimers in accordance with claim 1 wherein M is gallium.

5. Alkoxy-bridged metallophthalocyanine dimers in accordance with claim 1 wherein M is indium.

6. Alkoxy-bridged metallophthalocyanine dimers in accordance with claim 1 wherein R is ethyl, propyl, butyl, pentyl or hexyl.

7. The alkoxy-bridged metallophthalocyanine dimers 1,2-di(oxoaluminum phthalocyaninyl) ethane, 1,2-di(oxogallium phthalocyaninyl) ethane, 1,2-di(oxoindium phthalocyaninyl) ethane, 1,3-di(oxoaluminum phthalocyaninyl) propane, 1,3-di(oxogallium phthalocyaninyl) propane, 1,3-di(oxoindium phthalocyaninyl) propane, 1,2-di(oxoaluminum phthalocyaninyl) propane, 1,2-di(oxogallium phthalocyaninyl) propane, or 1,2-di(oxoindium phthalocyaninyl) propane.

8. 1,2-Di(oxogallium phthalocyaninyl) ethane which is an alkoxy-bridged gallium phthalocyanine dimer of the formula $C_{32}H_{16}N_8GaOCH_2CH_2OGaN_8H_{16}C_{32}$ with an X-ray diffraction pattern having major peaks at Bragg angles of: 6.7, 8.9, 12.8, 13.9, 15.7, 16.6, 21.2, 25.3, 25.9, 28.3, and the highest peak at 6.7 degrees 2Θ (2 theta +/−0.2°), and an infrared spectrum with major peaks at: 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 $cm^{-1}$.

9. An alkoxy-bridged metallophthalocyanine dimer of the formula

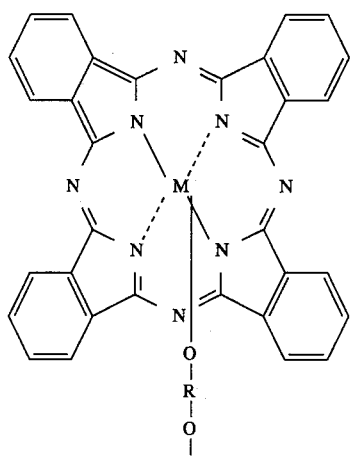

-continued

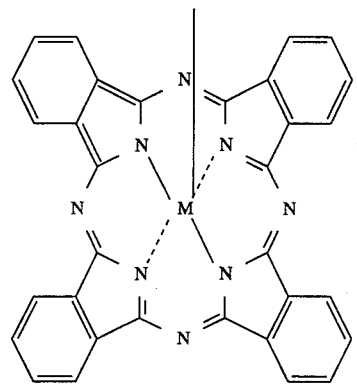

wherein M is a metal, and R is the aliphatic group alkyl.

10. An alkoxy-bridged metallophthalocyanine dimer in accordance with claim 1 wherein R is alkyl with 2 to about 12 carbon atoms.

11. An alkoxy-bridged metallophthalocyanine dimer in accordance with claim 2 wherein R is alkyl with 2 to about 12 carbon atoms.

12. An alkoxy-bridged metallophthalocyanine dimer accordance with claim 1 wherein R is ethyl.

13. An alkoxy-bridged metallophthalocyanine dimer in accordance with claim 1 wherein said alkyl ether contains an alkyl group with from 1 to about 20 carbon atoms.

14. An alkoxy-bridged metallophthalocyanine dimer in accordance with claim 1 wherein said alkyl ether contains an alkyl group with from 2 to about 6 carbon atoms.

15. An alkoxy-bridged metallophthalocyanine dimer in accordance with claim 9 wherein alkyl contains from 2 to about 16 carbon atoms.

16. An alkoxy-bridged metallophthalocyanine dimer in accordance with claim 9 wherein alkyl contains from 2 to about 12 carbon atoms.

17. An alkoxy-bridged metallophthalocyanine dimer in accordance with claim 9 wherein M is a trivalent metal of aluminum, gallium or indium, or a trivalent transition metal of Fe(III), Cr(III), Co(III), Mn(III), Ni(III), or V(III), and R is selected from the group consisting of:

—(CH₂)ₙ—  wherein n is from about 2 to about 12

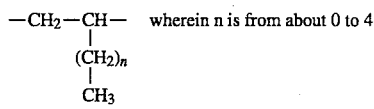  wherein n is from about 0 to 4

—CH₂—CH—CH₂—  wherein n is from about 0 to 4
      |
    (CH₂)ₙ
      |
     CH₃

—[(CH₂)ₘ—O—(CH₂)ₘ]ₙ—  wherein n is from about 1 to about 4, and m is from about 2 to about 4

—[CH(CH₃)CH₂—O—CH₂(CH₃)CH]ₙ—  wherein n is from about 1 to about 3.

wherein n is from about 1 to about 3.

18. An alkoxy-bridged metallophthalocyanine dimer of the formula $C_{32}H_{16}N_8MOROMN_8H_{16}C_{32}$ wherein M is a trivalent metal, and R is an alkyl group.

19. An alkoxy-bridged metallophthalocyanine dimer in accordance with claim 18 wherein R contains 2 to about 12 carbon atoms, M is a metal, and R is the aliphatic group alkyl.

20. An alkoxy-bridged metallophthalocyanine dimer in accordance with claim 18 wherein M is a metal, and R is the aliphatic group alkyl.

21. An alkoxy-bridged metallophthalocyanine in accordance with claim 1 wherein the O-R-O is derived from ethylene glycol.

22. An alkoxy-bridged metallophthalocyanine in accordance with claim 1 wherein R is alkyl.

23. Alkoxy-bridged metallophthalocyanine dimers of the formula $C_{32}H_{16}N_8MOROMN_8H_{16}C_{32}$ wherein M is a metal and R is an alkyl group.

* * * * *